US010258681B2

(12) United States Patent
Locht et al.

(10) Patent No.: US 10,258,681 B2
(45) **Date of Patent: *Apr. 16, 2019**

(54) ATTENUATED BORDETELLA STRAINS

(71) Applicants: Institut Pasteur de Lille, Lille (FR); Institut National de la Santé et de la Recherche Médicale (INSERM), Paris (FR)

(72) Inventors: Camille Locht, Brussels (BE); Nathalie Mielcarek, Blandain (BE); Anne-Sophie Debrie, La Madeleine (FR); Dominique Raze, Gruson (FR); Julie Bertout, Pont-à-Marcq (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,331

(22) Filed: Jun. 19, 2017

(65) Prior Publication Data

US 2017/0290903 A1 Oct. 12, 2017

Related U.S. Application Data

(60) Continuation of application No. 14/860,210, filed on Sep. 21, 2015, now Pat. No. 9,730,995, which is a continuation of application No. 14/658,817, filed on Mar. 16, 2015, now Pat. No. 9,180,178, which is a division of application No. 12/224,895, filed as application No. PCT/EP2007/001942 on Mar. 7, 2007, now Pat. No. 9,119,804.

(60) Provisional application No. 60/817,430, filed on Jun. 30, 2006, provisional application No. 60/780,827, filed on Mar. 10, 2006.

(51) Int. Cl.
*A61K 39/00* (2006.01)
*A61K 39/02* (2006.01)

(52) U.S. Cl.
CPC ...... *A61K 39/099* (2013.01); *A61K 2039/522* (2013.01); *A61K 2039/523* (2013.01); *A61K 2039/543* (2013.01)

(58) Field of Classification Search
None
See application file for complete search history.

(56) References Cited

U.S. PATENT DOCUMENTS

| | | | | |
|---|---|---|---|---|
| 5,215,739 A * | 6/1993 | Kamishita | A61K 9/0014 424/434 |
| 6,660,261 B1 | 12/2003 | Mielcarek | |
| 9,119,804 B2 * | 9/2015 | Locht | A61K 39/099 |
| 9,730,995 B2 * | 8/2017 | Locht | A61K 39/099 |

FOREIGN PATENT DOCUMENTS

WO 03/102170 * 12/2003

OTHER PUBLICATIONS

Stevenson et al FEMS Immunology and Medical Microbiology 37:121-128, 2003).*
Mameli et al (Expert Opinion on Biological Therapy 18(1):1-5, 2018).*
Coppens et al (Infection and Immunity, 69(9):5440-5446, 2001).*
English Translation of WO 03/102170.*
Srigley et al (Clinical Microbiology Newsletter 37(8):61-65, 2015).*
Zeddeman, A. et al: "Investigations into the emergence of pertactin-deficient Bordetella pertussis isolates in six European countries, 1996 to 2012," Research Articles, Aug. 21, 2014, pp. 1-11; «www.eurosurveillance.org.».
Thorstensson, R. et al: "A Phase I Clinical Study of a Live Attenuated Bordetella pertussis vaccine—BPZE1; A Single Centre, Double-Blind, Placebo-Controlled, Dose-Escalating Study of BPZE1 Given intranasally to healthy adult male volunteers," PLOS ONE, Jan. 2014, vol. 9, No. 1:10.

* cited by examiner

*Primary Examiner* — Patricia Duffy
(74) *Attorney, Agent, or Firm* — Stanley A. Kim

(57) ABSTRACT

A mutated *Bordetella* strain comprising at least a mutated ptx gene, a deleted or mutated dnt gene and a heterologous ampG gene is provided. The attenuated mutated *Bordetella* strain can be used in an immunogenic composition or a vaccine for the treatment or prevention of a *Bordetella* infection. Use of the attenuated *Bordetella* strain for the manufacture of a vaccine or immunogenic composition, as well as methods for protecting mammals against infection by *Bordetella* are also provided.

6 Claims, 14 Drawing Sheets

Specification includes a Sequence Listing.

Islet-activating protein S1 (NP_882282)

MRCTRAIRQTARTGWLTWLAILAVTAPVTSPAWADDPPATVYRYDSRPPEDVF
QNGFTAWGNNDNVLDHLTGRSCQVGSSNSAFVSTSSSRRYTEVYLEHRMQEAV
EAERAGRGTGHFIGYIYEVRADNNFYGAASSYFEYVDTYGDNAGRILAGALAT
YQSEYLAHRRIPPENIRRVTRVYHNGITGETTTTEYSNARYVSQQTRANPNPY
TSRRSVASIVGTLVRMAPVIGACMARQAESSEAMAAWSERAGEAMVLVYYESI
AYSF

Fig. 11

Dermonecrotic toxin (NP_881965)

MDKDESALRQLVDMALVGYDGVVEELLALPSEESGDLAGGRAKREKAEFALFS
EAPNGDEPIGQDARTWFYFPKYRPVAVSNLKKMQVAIRARLEPESLILQWLIA
LDVYLGVLIAALSRTVISDLVFEYVKARYEIYYLLNRVPHPLATAYLKRRRQR
PVDRSGRLGSVFEHPLWFAYDELAGTVDLDADIYEQALAESIERRMDGEPDDG
SLDTAEHDVWRLCRDGINRGEQAIFQASGPYGVVADAGYMRTVADLAYADALA
DCLHAQLRIRAQGSVDSPGDEMPRKLDAWEIAKFHLAATQQARVDLLEAAFAL
DYAALRDVRVYGDYRNALALRFIKREALRLLGARRGNASTMPAVAAGEYDEIV
ASGAANDAAYVSMAAALIAGVLCDLESAQRTLPVVLARFRPLGVLARFRRLEQ
ETAGMLLGDQEPEPRGFISFTDFRDSDAFASYAEYAAQFNDYIDQYSILEAQR
LARILALGSRMTVDQWCLPLQKVRHYKVLTSQPGLIARGIENHNRGIEYCLGR
PPLTDLPGLFTMFQLHDSSWLLVSNINGELWSDVLANAEVMQNPTLAALAEPQ
GRFRTGRRTGGWFLGGPATEGPSLRDNYLLKLRQSNPGLDVKKCWYFGYRQEY
RLPAGALGVPLFAVSVALRHSLDDLAAHAKSALYKPSEWQKFAFWIVPFYREI
FFSTQDRSYRVDVGSIVFDSISLLASVFSIGGKLGSFTRTQYGNLRNFVVRQR
IAGLSGQRLWRSVLKELPALIGASGLRLSRSLLVDLYEIFEPVPIRRLVAGFV
SATTVGGRNQAFLRQAFSAASSSAGRTGGQLASEWRMAGVDATGLVESTSGGR
FEGIYTRGLGPLSECTEHFIVESGNAYRVIWDAYTHGWRVVNGRLPPRLTYTV
PVRLNGQGHWETHLDVPGRGGAPEIFGRIRTRNLVALAAEQAAPMRRLLNQAR
RVALRHIDTCRSRLALPRAESDMDAAIRIFFGEPDAGLRQRIGRRLQEVRAYI
GDLSPVNDVLYRAGYDLDDVATLFNAVDRNTSLGRQARMELYLDAIVDLHARL
GYENARFVDLMAFHLLSLGHAATASEVVEAVSPRLLGNVFDISNVAQLERGIG
NPASTGLFVMLGAYSESSPAIFQSFVNDIFPAWRQASGGGPLVWNFGPAAISP
TRLDYANTDIGLLNHGDISPLRARPPLGGRRDIDLPPGLDISFVRYDRPVRMS
APRALDASVFRPVDGPVHGYIQSWTGAEIEYAYGAPAAAREVMLTDNVRIISI
ENGDEGAIGVRVRLDTVPVATPLILTGGSLSGCTTMVGVKEGYLAFYHTGKST
ELGDWATAREGVQALYQAHLAMGYAPISIPAPMRNDDLVSIAATYDRAVIAYL
GKDVPGGGSTRITRHDEGAGSVVSFDYNAAVQASAVPRLGQVYVLISNDGQGA
RAVLLAEDLAWAGSGSALDVLNERLVTLFPAPV

Fig. 12

AmpG protein (NP_878961.1)

MAPLLVLGFASGLPLALSSGTLQAWATVENVSLQSIGFLTLAGTAYTLKFLWA
PLIDRYVPPFLGRRRGWMLLTQVLLAAAIMVMGMLSPGSALLPLALVAVLVAF
LSASQDIAFDAYSTDVLRQEERGAGAAMRVMGYRLAMIVSGGLALIVADRWLG
WGNTYVLMGGLMLACALGTLWAPEPERPANPPRDLGAAVVEPFREFFSRRGAI
DMLLLIVLYKLGDAFAGALSTTFLLRGAGFSATEVGTVNKVLGLAATIVGALA
GGSIMTRWGLYRSLMAFGLLQAVSNLGYWLIAVSPKNLYLMGLAVGVENLCGG
LGTASFVALLMAMCRQQFSATQFALLSALAAVGRTYLAGPLTPVLVEWLDWPG
FFIVTVLIALPGLWLLRLRRNVIDELDAQTAR

Fig. 13

AmpG protein (NP_752478.1)

MSSQYLRIFQQPRSAILLILGFASGLPLALTSGTLQAWMTVENIDLKTIGFFS
LVGQAYVFKFLWSPLMDRYTPPFFGRRRGWLLATQILLLVAIAAMGFLEPGTQ
LRWMAALAVVIAFCSASQDIVFDAWKTDVLPAEERGAGAAISVLGYRLGMLVS
GGLALWLADKWLGWQGMYWLMAALLIPCIIATLLAPEPTDTIPVPKTLEQAVV
APLRDFFGRNNAWLILLLIVLYKLGDAFAMSLTTTFLIRGVGFDAGEVGVVNK
TLGLLATIVGALYGGILMQRLSLFRALLIFGILQGASNAGYWLLSITDKHLYS
MGAAVFFENLCGGMGTSAFVALLMTLCNKSFSATQFALLSALSAVGRVYVGPV
AGWFVEAHGWSTFYLFSVAAAVPGLILLLVCRQTLEYTRVNDNFISRTEYPAG
YAFAMWTLAAGISLLAVWLLLLTMDALDLTHFSFLPALLEVGVLVALSGVVLG
GLLDYLALRKTHLM

Fig. 14

SEQUENCE LISTING

```
<160> NUMBER OF SEQ ID NOS: 13

<210> SEQ ID NO 1
<211> LENGTH: 269
<212> TYPE: PRT
<213> ORGANISM: Bordetella pertussis

<400> SEQUENCE: 1

Met Arg Cys Thr Arg Ala Ile Arg Gln Thr Ala Arg Thr Gly Trp Leu
1               5                   10                  15

Thr Trp Leu Ala Ile Leu Ala Val Thr Ala Pro Val Thr Ser Pro Ala
            20                  25                  30

Trp Ala Asp Asp Pro Pro Ala Thr Val Tyr Arg Tyr Asp Ser Arg Pro
        35                  40                  45

Pro Glu Asp Val Phe Gln Asn Gly Phe Thr Ala Trp Gly Asn Asn Asp
    50                  55                  60

Asn Val Leu Asp His Leu Thr Gly Arg Ser Cys Gln Val Gly Ser Ser
65                  70                  75                  80

Asn Ser Ala Phe Val Ser Thr Ser Ser Ser Arg Arg Tyr Thr Glu Val
                85                  90                  95

Tyr Leu Glu His Arg Met Gln Glu Ala Val Glu Ala Glu Arg Ala Gly
            100                 105                 110

Arg Gly Thr Gly His Phe Ile Gly Tyr Ile Tyr Glu Val Arg Ala Asp
```

```
        115                 120                 125

Asn Asn Phe Tyr Gly Ala Ala Ser Ser Tyr Phe Glu Tyr Val Asp Thr
    130                 135                 140

Tyr Gly Asp Asn Ala Gly Arg Ile Leu Ala Gly Ala Leu Ala Thr Tyr
145                 150                 155                 160

Gln Ser Glu Tyr Leu Ala His Arg Arg Ile Pro Pro Glu Asn Ile Arg
                165                 170                 175

Arg Val Thr Arg Val Tyr His Asn Gly Ile Thr Gly Glu Thr Thr Thr
            180                 185                 190

Thr Glu Tyr Ser Asn Ala Arg Tyr Val Ser Gln Gln Thr Arg Ala Asn
        195                 200                 205

Pro Asn Pro Tyr Thr Ser Arg Arg Ser Val Ala Ser Ile Val Gly Thr
    210                 215                 220

Leu Val Arg Met Ala Pro Val Ile Gly Ala Cys Met Ala Arg Gln Ala
225                 230                 235                 240

Glu Ser Ser Glu Ala Met Ala Ala Trp Ser Glu Arg Ala Gly Glu Ala
                245                 250                 255

Met Val Leu Val Tyr Tyr Glu Ser Ile Ala Tyr Ser Phe
            260                 265


<210> SEQ ID NO 2
<211> LENGTH: 1464
<212> TYPE: PRT
<213> ORGANISM: Bordetella pertussis

<400> SEQUENCE: 2

Met Asp Lys Asp Glu Ser Ala Leu Arg Gln Leu Val Asp Met Ala Leu
1               5                   10                  15

Val Gly Tyr Asp Gly Val Val Glu Glu Leu Leu Ala Leu Pro Ser Glu
            20                  25                  30

Glu Ser Gly Asp Leu Ala Gly Gly Arg Ala Lys Arg Glu Lys Ala Glu
        35                  40                  45

Phe Ala Leu Phe Ser Glu Ala Pro Asn Gly Asp Glu Pro Ile Gly Gln
    50                  55                  60

Asp Ala Arg Thr Trp Phe Tyr Phe Pro Lys Tyr Arg Pro Val Ala Val
65                  70                  75                  80

Ser Asn Leu Lys Lys Met Gln Val Ala Ile Arg Ala Arg Leu Glu Pro
                85                  90                  95

Glu Ser Leu Ile Leu Gln Trp Leu Ile Ala Leu Asp Val Tyr Leu Gly
            100                 105                 110

Val Leu Ile Ala Ala Leu Ser Arg Thr Val Ile Ser Asp Leu Val Phe
        115                 120                 125

Glu Tyr Val Lys Ala Arg Tyr Glu Ile Tyr Tyr Leu Leu Asn Arg Val
    130                 135                 140

Pro His Pro Leu Ala Thr Ala Tyr Leu Lys Arg Arg Arg Gln Arg Pro
145                 150                 155                 160

Val Asp Arg Ser Gly Arg Leu Gly Ser Val Phe Glu His Pro Leu Trp
                165                 170                 175

Phe Ala Tyr Asp Glu Leu Ala Gly Thr Val Asp Leu Asp Ala Asp Ile
            180                 185                 190

Tyr Glu Gln Ala Leu Ala Glu Ser Ile Glu Arg Arg Met Asp Gly Glu
        195                 200                 205

Pro Asp Asp Gly Ser Leu Asp Thr Ala Glu His Asp Val Trp Arg Leu
    210                 215                 220
```

-continued

```
Cys Arg Asp Gly Ile Asn Arg Gly Glu Gln Ala Ile Phe Gln Ala Ser
225                 230                 235                 240

Gly Pro Tyr Gly Val Val Ala Asp Ala Gly Tyr Met Arg Thr Val Ala
                245                 250                 255

Asp Leu Ala Tyr Ala Asp Ala Leu Ala Asp Cys Leu His Ala Gln Leu
            260                 265                 270

Arg Ile Arg Ala Gln Gly Ser Val Asp Ser Pro Gly Asp Glu Met Pro
        275                 280                 285

Arg Lys Leu Asp Ala Trp Glu Ile Ala Lys Phe His Leu Ala Ala Thr
    290                 295                 300

Gln Gln Ala Arg Val Asp Leu Leu Glu Ala Ala Phe Ala Leu Asp Tyr
305                 310                 315                 320

Ala Ala Leu Arg Asp Val Arg Val Tyr Gly Asp Tyr Arg Asn Ala Leu
                325                 330                 335

Ala Leu Arg Phe Ile Lys Arg Glu Ala Leu Arg Leu Leu Gly Ala Arg
            340                 345                 350

Arg Gly Asn Ala Ser Thr Met Pro Ala Val Ala Ala Gly Glu Tyr Asp
        355                 360                 365

Glu Ile Val Ala Ser Gly Ala Ala Asn Asp Ala Ala Tyr Val Ser Met
    370                 375                 380

Ala Ala Ala Leu Ile Ala Gly Val Leu Cys Asp Leu Glu Ser Ala Gln
385                 390                 395                 400

Arg Thr Leu Pro Val Val Leu Ala Arg Phe Arg Pro Leu Gly Val Leu
                405                 410                 415

Ala Arg Phe Arg Arg Leu Glu Gln Glu Thr Ala Gly Met Leu Leu Gly
            420                 425                 430

Asp Gln Glu Pro Glu Pro Arg Gly Phe Ile Ser Phe Thr Asp Phe Arg
        435                 440                 445

Asp Ser Asp Ala Phe Ala Ser Tyr Ala Glu Tyr Ala Ala Gln Phe Asn
    450                 455                 460

Asp Tyr Ile Asp Gln Tyr Ser Ile Leu Glu Ala Gln Arg Leu Ala Arg
465                 470                 475                 480

Ile Leu Ala Leu Gly Ser Arg Met Thr Val Asp Gln Trp Cys Leu Pro
                485                 490                 495

Leu Gln Lys Val Arg His Tyr Lys Val Leu Thr Ser Gln Pro Gly Leu
            500                 505                 510

Ile Ala Arg Gly Ile Glu Asn His Asn Arg Gly Ile Glu Tyr Cys Leu
        515                 520                 525

Gly Arg Pro Pro Leu Thr Asp Leu Pro Gly Leu Phe Thr Met Phe Gln
    530                 535                 540

Leu His Asp Ser Ser Trp Leu Leu Val Ser Asn Ile Asn Gly Glu Leu
545                 550                 555                 560

Trp Ser Asp Val Leu Ala Asn Ala Glu Val Met Gln Asn Pro Thr Leu
                565                 570                 575

Ala Ala Leu Ala Glu Pro Gln Gly Arg Phe Arg Thr Gly Arg Arg Thr
            580                 585                 590

Gly Gly Trp Phe Leu Gly Gly Pro Ala Thr Glu Gly Pro Ser Leu Arg
        595                 600                 605

Asp Asn Tyr Leu Leu Lys Leu Arg Gln Ser Asn Pro Gly Leu Asp Val
    610                 615                 620

Lys Lys Cys Trp Tyr Phe Gly Tyr Arg Gln Glu Tyr Arg Leu Pro Ala
625                 630                 635                 640

Gly Ala Leu Gly Val Pro Leu Phe Ala Val Ser Val Ala Leu Arg His
```

-continued

```
                645                 650                 655

Ser Leu Asp Asp Leu Ala Ala His Ala Lys Ser Ala Leu Tyr Lys Pro
            660                 665                 670

Ser Glu Trp Gln Lys Phe Ala Phe Trp Ile Val Pro Phe Tyr Arg Glu
        675                 680                 685

Ile Phe Phe Ser Thr Gln Asp Arg Ser Tyr Arg Val Asp Val Gly Ser
    690                 695                 700

Ile Val Phe Asp Ser Ile Ser Leu Leu Ala Ser Val Phe Ser Ile Gly
705                 710                 715                 720

Gly Lys Leu Gly Ser Phe Thr Arg Thr Gln Tyr Gly Asn Leu Arg Asn
                725                 730                 735

Phe Val Val Arg Gln Arg Ile Ala Gly Leu Ser Gly Gln Arg Leu Trp
            740                 745                 750

Arg Ser Val Leu Lys Glu Leu Pro Ala Leu Ile Gly Ala Ser Gly Leu
        755                 760                 765

Arg Leu Ser Arg Ser Leu Leu Val Asp Leu Tyr Glu Ile Phe Glu Pro
    770                 775                 780

Val Pro Ile Arg Arg Leu Val Ala Gly Phe Val Ser Ala Thr Thr Val
785                 790                 795                 800

Gly Gly Arg Asn Gln Ala Phe Leu Arg Gln Ala Phe Ser Ala Ala Ser
                805                 810                 815

Ser Ser Ala Gly Arg Thr Gly Gly Gln Leu Ala Ser Glu Trp Arg Met
            820                 825                 830

Ala Gly Val Asp Ala Thr Gly Leu Val Glu Ser Thr Ser Gly Gly Arg
        835                 840                 845

Phe Glu Gly Ile Tyr Thr Arg Gly Leu Gly Pro Leu Ser Glu Cys Thr
    850                 855                 860

Glu His Phe Ile Val Glu Ser Gly Asn Ala Tyr Arg Val Ile Trp Asp
865                 870                 875                 880

Ala Tyr Thr His Gly Trp Arg Val Val Asn Gly Arg Leu Pro Pro Arg
                885                 890                 895

Leu Thr Tyr Thr Val Pro Val Arg Leu Asn Gly Gln Gly His Trp Glu
            900                 905                 910

Thr His Leu Asp Val Pro Gly Arg Gly Gly Ala Pro Glu Ile Phe Gly
        915                 920                 925

Arg Ile Arg Thr Arg Asn Leu Val Ala Leu Ala Ala Glu Gln Ala Ala
    930                 935                 940

Pro Met Arg Arg Leu Leu Asn Gln Ala Arg Arg Val Ala Leu Arg His
945                 950                 955                 960

Ile Asp Thr Cys Arg Ser Arg Leu Ala Leu Pro Arg Ala Glu Ser Asp
                965                 970                 975

Met Asp Ala Ala Ile Arg Ile Phe Phe Gly Glu Pro Asp Ala Gly Leu
            980                 985                 990

Arg Gln Arg Ile Gly Arg Arg Leu  Gln Glu Val Arg Ala  Tyr Ile Gly
        995                 1000                1005

Asp Leu  Ser Pro Val Asn Asp  Val Leu Tyr Arg Ala  Gly Tyr Asp
    1010                1015                1020

Leu Asp  Asp Val Ala Thr Leu  Phe Asn Ala Val Asp  Arg Asn Thr
    1025                1030                1035

Ser Leu  Gly Arg Gln Ala Arg  Met Glu Leu Tyr Leu  Asp Ala Ile
    1040                1045                1050

Val Asp  Leu His Ala Arg Leu  Gly Tyr Glu Asn Ala  Arg Phe Val
    1055                1060                1065
```

-continued

```
Asp Leu  Met Ala Phe His Leu  Leu Ser Leu Gly His  Ala Ala Thr
    1070                 1075                 1080

Ala Ser  Glu Val Val Glu Ala  Val Ser Pro Arg Leu  Leu Gly Asn
    1085                 1090                 1095

Val Phe  Asp Ile Ser Asn Val  Ala Gln Leu Glu Arg  Gly Ile Gly
    1100                 1105                 1110

Asn Pro  Ala Ser Thr Gly Leu  Phe Val Met Leu Gly  Ala Tyr Ser
    1115                 1120                 1125

Glu Ser  Ser Pro Ala Ile Phe  Gln Ser Phe Val Asn  Asp Ile Phe
    1130                 1135                 1140

Pro Ala  Trp Arg Gln Ala Ser  Gly Gly Gly Pro Leu  Val Trp Asn
    1145                 1150                 1155

Phe Gly  Pro Ala Ala Ile Ser  Pro Thr Arg Leu Asp  Tyr Ala Asn
    1160                 1165                 1170

Thr Asp  Ile Gly Leu Leu Asn  His Gly Asp Ile Ser  Pro Leu Arg
    1175                 1180                 1185

Ala Arg  Pro Pro Leu Gly Gly  Arg Arg Asp Ile Asp  Leu Pro Pro
    1190                 1195                 1200

Gly Leu  Asp Ile Ser Phe Val  Arg Tyr Asp Arg Pro  Val Arg Met
    1205                 1210                 1215

Ser Ala  Pro Arg Ala Leu Asp  Ala Ser Val Phe Arg  Pro Val Asp
    1220                 1225                 1230

Gly Pro  Val His Gly Tyr Ile  Gln Ser Trp Thr Gly  Ala Glu Ile
    1235                 1240                 1245

Glu Tyr  Ala Tyr Gly Ala Pro  Ala Ala Ala Arg Glu  Val Met Leu
    1250                 1255                 1260

Thr Asp  Asn Val Arg Ile Ile  Ser Ile Glu Asn Gly  Asp Glu Gly
    1265                 1270                 1275

Ala Ile  Gly Val Arg Val Arg  Leu Asp Thr Val Pro  Val Ala Thr
    1280                 1285                 1290

Pro Leu  Ile Leu Thr Gly Gly  Ser Leu Ser Gly Cys  Thr Thr Met
    1295                 1300                 1305

Val Gly  Val Lys Glu Gly Tyr  Leu Ala Phe Tyr His  Thr Gly Lys
    1310                 1315                 1320

Ser Thr  Glu Leu Gly Asp Trp  Ala Thr Ala Arg Glu  Gly Val Gln
    1325                 1330                 1335

Ala Leu  Tyr Gln Ala His Leu  Ala Met Gly Tyr Ala  Pro Ile Ser
    1340                 1345                 1350

Ile Pro  Ala Pro Met Arg Asn  Asp Asp Leu Val Ser  Ile Ala Ala
    1355                 1360                 1365

Thr Tyr  Asp Arg Ala Val Ile  Ala Tyr Leu Gly Lys  Asp Val Pro
    1370                 1375                 1380

Gly Gly  Gly Ser Thr Arg Ile  Thr Arg His Asp Glu  Gly Ala Gly
    1385                 1390                 1395

Ser Val  Val Ser Phe Asp Tyr  Asn Ala Ala Val Gln  Ala Ser Ala
    1400                 1405                 1410

Val Pro  Arg Leu Gly Gln Val  Tyr Val Leu Ile Ser  Asn Asp Gly
    1415                 1420                 1425

Gln Gly  Ala Arg Ala Val Leu  Leu Ala Glu Asp Leu  Ala Trp Ala
    1430                 1435                 1440

Gly Ser  Gly Ser Ala Leu Asp  Val Leu Asn Glu Arg  Leu Val Thr
    1445                 1450                 1455
```

```
Leu Phe  Pro Ala Pro Val
    1460


<210> SEQ ID NO 3
<211> LENGTH: 403
<212> TYPE: PRT
<213> ORGANISM: Bordetella pertussis

<400> SEQUENCE: 3

Met Ala Pro Leu Leu Val Leu Gly Phe Ala Ser Gly Leu Pro Leu Ala
1               5                   10                  15

Leu Ser Ser Gly Thr Leu Gln Ala Trp Ala Thr Val Glu Asn Val Ser
            20                  25                  30

Leu Gln Ser Ile Gly Phe Leu Thr Leu Ala Gly Thr Ala Tyr Thr Leu
        35                  40                  45

Lys Phe Leu Trp Ala Pro Leu Ile Asp Arg Tyr Val Pro Pro Phe Leu
    50                  55                  60

Gly Arg Arg Arg Gly Trp Met Leu Leu Thr Gln Val Leu Leu Ala Ala
65                  70                  75                  80

Ala Ile Met Val Met Gly Met Leu Ser Pro Gly Ser Ala Leu Leu Pro
                85                  90                  95

Leu Ala Leu Val Ala Val Leu Val Ala Phe Leu Ser Ala Ser Gln Asp
            100                 105                 110

Ile Ala Phe Asp Ala Tyr Ser Thr Asp Val Leu Arg Gln Glu Glu Arg
        115                 120                 125

Gly Ala Gly Ala Ala Met Arg Val Met Gly Tyr Arg Leu Ala Met Ile
    130                 135                 140

Val Ser Gly Gly Leu Ala Leu Ile Val Ala Asp Arg Trp Leu Gly Trp
145                 150                 155                 160

Gly Asn Thr Tyr Val Leu Met Gly Gly Leu Met Leu Ala Cys Ala Leu
                165                 170                 175

Gly Thr Leu Trp Ala Pro Glu Pro Glu Arg Pro Ala Asn Pro Pro Arg
            180                 185                 190

Asp Leu Gly Ala Ala Val Val Glu Pro Phe Arg Glu Phe Phe Ser Arg
        195                 200                 205

Arg Gly Ala Ile Asp Met Leu Leu Leu Ile Val Leu Tyr Lys Leu Gly
    210                 215                 220

Asp Ala Phe Ala Gly Ala Leu Ser Thr Thr Phe Leu Leu Arg Gly Ala
225                 230                 235                 240

Gly Phe Ser Ala Thr Glu Val Gly Thr Val Asn Lys Val Leu Gly Leu
                245                 250                 255

Ala Ala Thr Ile Val Gly Ala Leu Ala Gly Gly Ser Ile Met Thr Arg
            260                 265                 270

Trp Gly Leu Tyr Arg Ser Leu Met Ala Phe Gly Leu Leu Gln Ala Val
        275                 280                 285

Ser Asn Leu Gly Tyr Trp Leu Ile Ala Val Ser Pro Lys Asn Leu Tyr
    290                 295                 300

Leu Met Gly Leu Ala Val Gly Val Glu Asn Leu Cys Gly Gly Leu Gly
305                 310                 315                 320

Thr Ala Ser Phe Val Ala Leu Leu Met Ala Met Cys Arg Gln Gln Phe
                325                 330                 335

Ser Ala Thr Gln Phe Ala Leu Leu Ser Ala Leu Ala Ala Val Gly Arg
            340                 345                 350

Thr Tyr Leu Ala Gly Pro Leu Thr Pro Val Leu Val Glu Trp Leu Asp
        355                 360                 365
```

Trp Pro Gly Phe Phe Ile Val Thr Val Leu Ile Ala Leu Pro Gly Leu
    370                 375                 380

Trp Leu Leu Arg Leu Arg Arg Asn Val Ile Asp Glu Leu Asp Ala Gln
385                 390                 395                 400

Thr Ala Arg

<210> SEQ ID NO 4
<211> LENGTH: 491
<212> TYPE: PRT
<213> ORGANISM: Escherichia coli

<400> SEQUENCE: 4

Met Ser Ser Gln Tyr Leu Arg Ile Phe Gln Gln Pro Arg Ser Ala Ile
1               5                   10                  15

Leu Leu Ile Leu Gly Phe Ala Ser Gly Leu Pro Leu Ala Leu Thr Ser
            20                  25                  30

Gly Thr Leu Gln Ala Trp Met Thr Val Glu Asn Ile Asp Leu Lys Thr
        35                  40                  45

Ile Gly Phe Phe Ser Leu Val Gly Gln Ala Tyr Val Phe Lys Phe Leu
    50                  55                  60

Trp Ser Pro Leu Met Asp Arg Tyr Thr Pro Pro Phe Phe Gly Arg Arg
65                  70                  75                  80

Arg Gly Trp Leu Leu Ala Thr Gln Ile Leu Leu Leu Val Ala Ile Ala
                85                  90                  95

Ala Met Gly Phe Leu Glu Pro Gly Thr Gln Leu Arg Trp Met Ala Ala
            100                 105                 110

Leu Ala Val Val Ile Ala Phe Cys Ser Ala Ser Gln Asp Ile Val Phe
        115                 120                 125

Asp Ala Trp Lys Thr Asp Val Leu Pro Ala Glu Glu Arg Gly Ala Gly
    130                 135                 140

Ala Ala Ile Ser Val Leu Gly Tyr Arg Leu Gly Met Leu Val Ser Gly
145                 150                 155                 160

Gly Leu Ala Leu Trp Leu Ala Asp Lys Trp Leu Gly Trp Gln Gly Met
                165                 170                 175

Tyr Trp Leu Met Ala Ala Leu Leu Ile Pro Cys Ile Ile Ala Thr Leu
            180                 185                 190

Leu Ala Pro Glu Pro Thr Asp Thr Ile Pro Val Pro Lys Thr Leu Glu
        195                 200                 205

Gln Ala Val Val Ala Pro Leu Arg Asp Phe Phe Gly Arg Asn Asn Ala
    210                 215                 220

Trp Leu Ile Leu Leu Leu Ile Val Leu Tyr Lys Leu Gly Asp Ala Phe
225                 230                 235                 240

Ala Met Ser Leu Thr Thr Thr Phe Leu Ile Arg Gly Val Gly Phe Asp
                245                 250                 255

Ala Gly Glu Val Gly Val Val Asn Lys Thr Leu Gly Leu Leu Ala Thr
            260                 265                 270

Ile Val Gly Ala Leu Tyr Gly Gly Ile Leu Met Gln Arg Leu Ser Leu
        275                 280                 285

Phe Arg Ala Leu Leu Ile Phe Gly Ile Leu Gln Gly Ala Ser Asn Ala
    290                 295                 300

Gly Tyr Trp Leu Leu Ser Ile Thr Asp Lys His Leu Tyr Ser Met Gly
305                 310                 315                 320

Ala Ala Val Phe Phe Glu Asn Leu Cys Gly Gly Met Gly Thr Ser Ala
                325                 330                 335

-continued

```
Phe Val Ala Leu Leu Met Thr Leu Cys Asn Lys Ser Phe Ser Ala Thr
            340                 345                 350

Gln Phe Ala Leu Leu Ser Ala Leu Ser Ala Val Gly Arg Val Tyr Val
        355                 360                 365

Gly Pro Val Ala Gly Trp Phe Val Glu Ala His Gly Trp Ser Thr Phe
    370                 375                 380

Tyr Leu Phe Ser Val Ala Ala Ala Val Pro Gly Leu Ile Leu Leu Leu
385                 390                 395                 400

Val Cys Arg Gln Thr Leu Glu Tyr Thr Arg Val Asn Asp Asn Phe Ile
                405                 410                 415

Ser Arg Thr Glu Tyr Pro Ala Gly Tyr Ala Phe Ala Met Trp Thr Leu
            420                 425                 430

Ala Ala Gly Ile Ser Leu Leu Ala Val Trp Leu Leu Leu Leu Thr Met
        435                 440                 445

Asp Ala Leu Asp Leu Thr His Phe Ser Phe Leu Pro Ala Leu Leu Glu
    450                 455                 460

Val Gly Val Leu Val Ala Leu Ser Gly Val Val Leu Gly Gly Leu Leu
465                 470                 475                 480

Asp Tyr Leu Ala Leu Arg Lys Thr His Leu Met
                485                 490
```

<210> SEQ ID NO 5
<211> LENGTH: 32
<212> TYPE: DNA
<213> ORGANISM: Artificial
<220> FEATURE:
<223> OTHER INFORMATION: Oligonucleotide A

<400> SEQUENCE: 5
tataaatcga tattcctgct ggtttcgttc tc 32

<210> SEQ ID NO 6
<211> LENGTH: 30
<212> TYPE: DNA
<213> ORGANISM: Artificial
<220> FEATURE:
<223> OTHER INFORMATION: Oligonucleotide B

<400> SEQUENCE: 6
tatagctagc aagttgggaa acgacaccac 30

<210> SEQ ID NO 7
<211> LENGTH: 25
<212> TYPE: DNA
<213> ORGANISM: Artificial
<220> FEATURE:
<223> OTHER INFORMATION: Oligonucleotide C

<400> SEQUENCE: 7
taagaagcaa aataagccag gcatt 25

<210> SEQ ID NO 8
<211> LENGTH: 30
<212> TYPE: DNA
<213> ORGANISM: Artificial

-continued

```
<220> FEATURE:
<223> OTHER INFORMATION: Oligonucleotide D

<400> SEQUENCE: 8

tataccatgg cgccgctgct ggtgctgggc                                       30


<210> SEQ ID NO 9
<211> LENGTH: 30
<212> TYPE: DNA
<213> ORGANISM: Artificial
<220> FEATURE:
<223> OTHER INFORMATION: Oligonucleotide E

<400> SEQUENCE: 9

tatatctaga cgctggccgt aaccttagca                                       30


<210> SEQ ID NO 10
<211> LENGTH: 30
<212> TYPE: DNA
<213> ORGANISM: Artificial
<220> FEATURE:
<223> OTHER INFORMATION: Oligonucleotide F

<400> SEQUENCE: 10

tatagaattc gctcggttcg ctggtcaagg                                       30


<210> SEQ ID NO 11
<211> LENGTH: 30
<212> TYPE: DNA
<213> ORGANISM: Artificial
<220> FEATURE:
<223> OTHER INFORMATION: Oligonucleotide G

<400> SEQUENCE: 11

tatatctaga gcaatgccga ttcatcttta                                       30


<210> SEQ ID NO 12
<211> LENGTH: 30
<212> TYPE: DNA
<213> ORGANISM: Artificial
<220> FEATURE:
<223> OTHER INFORMATION: Oligonucleotide H

<400> SEQUENCE: 12

tatatctaga gcggccttta ttgcttttcc                                       30


<210> SEQ ID NO 13
<211> LENGTH: 30
<212> TYPE: DNA
<213> ORGANISM: Artificial
<220> FEATURE:
<223> OTHER INFORMATION: Oligonucleotide I

<400> SEQUENCE: 13

tataaagctt ctcatgcacg ccggcttctc                                       30
```

ATTENUATED BORDETELLA STRAINS

CROSS-REFERENCE TO RELATED APPLICATIONS

The present application is a continuation application of U.S. patent application Ser. No. 14/860,210 filed on Sep. 21, 2015, which is a continuation application of U.S. patent application Ser. No. 14/658,817 filed on Mar. 16, 2015 (now U.S. Pat. No. 9,180,178), which is a divisional application of U.S. nonprovisional patent application Ser. No. 12/224,895 filed on Nov. 19, 2008 (now U.S. Pat. No. 9,119,804) as a national stage entry application under 35 U.S.C. 371 of international patent application number PCT/EP/001942, filed on Mar. 7, 2007, which designated the U.S. and claims the priority of U.S. provisional patent application Ser. No. 60/817,430 filed on Jun. 30, 2006 and U.S. provisional patent application Ser. No. 60/780,827 filed on Mar. 10, 2006, which are incorporated herein by reference in their entirety.

FIELD OF THE INVENTION

The present invention relates to a mutated *Bordetella* strain comprising at least a mutated ptx gene, a deleted or mutated-dnt gene and a heterologous ampG gene. The attenuated mutated *Bordetella* strain can be used in an immunogenic composition or a vaccine for the treatment or prevention of a *Bordetella* infection. Use of the attenuated *Bordetella* strain for the manufacture of a vaccine or immunogenic compositions, as well as methods for protecting mammals against infection by *Bordetella* also form a part of the invention.

BACKGROUND OF THE INVENTION AND RELATED PRIOR ART

Pertussis is still among the principal causes of death world-wide, and its incidence is increasing even in countries with high vaccine coverage. Although all age groups are susceptible, it is most severe in infants too young to be protected by currently available vaccines.

Whooping cough or pertussis is a severe childhood disease responsible for high mortality rates before the introduction of effective vaccines in the second half of the 20th century. The success of these vaccines has led to the opinion that the disease is essentially under control, although worldwide 200,000 to 400,000 pertussis-linked deaths are still recorded annually, and the disease still ranks sixth among the causes of mortality due to infectious agents [1]. Although mostly prevalent in developing countries, the disease is also re-emerging in the developed world [2, 3], including the U.S.A., where the incidence has increased five-fold over the last twenty years [4]. Unexpectedly, the epidemiology of pertussis has changed in countries with high vaccine coverage, where cases of adolescent and adult pertussis are increasingly frequent [5]. This is probably due to progressive waning of vaccine-mediated immunity during adolescence. Often atypical and therefore difficult to diagnose, pertussis is generally not life-threatening in adults and in many cases remains unnoticed. However, infected adults constitute an important reservoir for transmission of the disease to very young children, too young to be fully vaccinated, and therefore at risk to develop severe disease associated with high mortality rates.

Pertussis vaccination usually begins at two months of age, and full protection requires at least three immunizations at one- to two-month intervals. Therefore, infants are not fully protected before the age of 6 months using the currently available vaccines. To reduce the incidence of pertussis in the very young and most vulnerable age groups, early immunization, possibly at birth, would thus be highly desirable. However, numerous studies in humans and in animal models have suggested that the neonatal immune system is too immature to effectively induce vaccine-mediated protective immunity [6, 7]. Especially the IFN-γ production, indicative of a Th1 response that is essential to the development of protective immunity to pertussis [8], appears to be significantly reduced in human newborns, compared to older children or adults [9]. This is also reflected by the fact that significant amounts of antigen-specific IFN-γ are only produced after several months (≥6 months) in children vaccinated with pertussis vaccines, especially with acellular vaccines (aPV) [10].

Natural infection with *Bordetella pertussis* has long been considered to induce strong and long-lasting immunity, that wanes much later than vaccine-induced immunity [5, 11]. Furthermore, infection with *B. pertussis* induces measurable antigen-specific Th1 type immune responses even in very young children (as young as one month of age) [12]. These observations suggest that live vaccines applicable by the nasal route in order to mimic as closely as possible natural infection, may be attractive alternatives over the currently available vaccines.

There are many vaccinating compositions to treat *Bordetella* infections known in the art. However, these immunogenic compositions are not used to treat newborn children or in cases where an epidemic and rapid protective immunity is required.

Thus, French Patent FR 0206666 discloses live *Bordetella* strains that have been rendered deficient in at least two toxins chosen from PTX, DNT, AC and TCT. This patent discloses the over expression of an endogenous ampG gene by the addition of a strong promoter, and the addition of 11 terminal amino acids of the ampG gene from *E. coli.*

Mielcarek et al, Vaccine (2006; 2452: 52154-52-55) disclose a strain of *Bordetella pertussis* attenuated of PTK, DTN- and TCr for use in the immunization of mice. This reference discloses that to reduce the production of tracheal cytotoxin, the ampG gene should be overexpressed. However, upon further evaluation, the authors realized that by over-expressing the ampG gene, there is an increase in tracheal cytotoxin and not a decrease as was originally thought.

Mielcarek et al in Advance Drug Delivery Review 51 (2001) pgs. 55-69 disclose that live vaccines can induce systemic and mucosal responses when administered by the oral or nasal route.

Roduit et al in Infection and Immunity (2002 July; 70(7): 3521-8) describe vaccinating neonatals and infants with mutated *Bordetella* strains with a DTP composition.

Mattoo et al, in Frontiers of Bioscience 6, e168-e186 (2001), suggest replacing the endogenous ampG gene in *Bordetella* with the *E. coli* ampG gene, which resulted in a decrease in the amount of TCT produced.

Thus, the prior art although disclosing various types of vaccinating compositions fails to address the problem of providing a vaccine or immunogenic composition that can provide protection to a newborn prior to six months. Furthermore, the prior art fails to disclose an immunogenic or a vaccine that provides rapid protective immunity against a *Bordetella* infection. The prior art also fails to disclose an immunogenic composition or vaccine that provides a rapid protective immunity against a *Bordetella* infection, said protective immunity increasing over at least the next two months following vaccination.

Therefore, it is an object of the present invention to overcome the deficiencies in the prior art.

It is another object of the present invention to produce a live attenuated vaccine candidate or immunogenic composition through genetic attenuation of a *Bordetella* strain such as *B. pertussis* or *B. parapertussis* to diminish pathogenicity, while maintaining the ability to colonize and induce protective immunity.

It is another object of the present invention to produce a vaccine or immunogenic composition that induces protection in newborns after a single intranasal administration that is superior to the protection provided by the current aPV.

It is yet another object of the present invention to provide protection against infection with *Bordetella parapertussis*, as well as *Bordetella pertussis* which was not seen after vaccination with aPV.

Another object of the present invention is to induce strong protective immunity in newborns against *Bordetella* infection.

Yet another object of the present invention is to provide a vaccine or immunogenic composition that induces mucosal and systemic immunity.

It is another object of the present invention to produce a live attenuated *Bordetella pertussis* strain to be given as a single-dose nasal vaccine in early life, called BPZE1.

It is yet another object of the present invention to provide a vaccine that can not only be used to vaccinate newborns, but can be used in all mammals of any age in the case of an epidemic of whooping cough.

Another object of the present invention is to provide a vaccine against *Bordetella* infection that induces a rapid protective immunity and/or a protective immunity that increases over at least the next two months after the vaccination.

Yet another object of the present invention is to provide prevention or treatment against *Bordetella* infection that is relatively low in production costs.

These and other objects are achieved by the present invention as evidenced by the summary of the invention, description of the preferred embodiments and the claims.

SUMMARY OF THE INVENTION

The present invention provides a mutated *Bordetella* strain comprising at least a mutated pertussis toxin (ptx) gene, a deleted or mutated dermonecrotic toxin (dnt) gene, and a heterologous ampG gene.

In another aspect the present invention relates to an immunogenic composition comprising a mutated *Bordetella* strain comprising at least a mutated pertussis toxin (ptx) gene, a deleted or mutated pertussis dermonecrotic toxin (dnt) gene, and a heterologous ampG gene.

In yet another aspect the present invention provides a vaccine comprising the attenuated *Bordetella* strain comprising at least a mutated pertussis toxin (ptx) gene, a deleted or mutated pertussis dermonecrotic toxin (dnt) gene, and a heterologous ampG gene.

In still another aspect, the present invention provides the use of an attenuated *Bordetella* strain comprising at least a mutated ptx gene, a deleted or mutated dnt gene, and a heterologous ampG gene for the manufacture of a vaccine for the prevention of a *Bordetella* infection.

In yet another aspect, the present invention provides the use of an attenuated *Bordetella* strain comprising at least a mutated ptx gene, a deleted or mutated dnt gene, and a heterologous ampG gene for the manufacture of a vaccine for the induction of an immune response directed preferentially toward the Th1 pathway against said attenuated *Bordetella*.

Also provided is a method of protecting a mammal against disease caused by infection by *Bordetella pertussis* and *Bordetella parapertussis* comprising administering to said mammal in need of such treatment a mutated *Bordetella* strain comprising at least a mutated ptx gene, a deleted or mutated dnt gene, and a heterologous ampG gene.

A method of providing a rapid protective immunity against a *Bordetella* infection comprising administering to said mammal in need of such treatment a mutated *Bordetella* strain comprising at least a mutated ptx gene, a deleted or mutated dnt gene, and a heterologous ampG gene is also part of the present invention.

A method of providing a rapid protective immunity against a *Bordetella* infection comprising administering to a mammal in need of such treatment a mutated *Bordetella* strain comprising at least a mutated ptx gene, a deleted or mutated dnt gene, and a heterologous ampG gene or a vaccine comprising said mutated *Bordetella* strain, wherein said method provides further an increase in said protective immunity over at least two months after vaccination is still another aspect of the present invention.

Use of the mutated *Bordetella* strain comprising at least a mutated ptx gene, a deleted or mutated dnt gene and a heterologous ampG gene for the preparation of a multivalent vaccine (i.e., a vaccine for preventing or treating infections caused by different pathogens) to treat respiratory diseases is yet another aspect of the present invention.

Use of an attenuated *Bordetella* strain of the invention, by administration to mammals in need of a rapid protective immunity against a *Bordetella* infection, wherein said protective immunity increases over at least two months after administration, is also part of the present invention.

A method to provide a mucosal response and a systemic response to treat or protect against *Bordetella* infections in mammals is still another aspect of the present invention.

BRIEF DESCRIPTION OF THE DRAWINGS

FIG. 11 is the amino acid sequence of pertussis toxin (SEQ 10 NO:1) (islet-activating protein S1). The first 34 amino acids are the signal sequence, while amino acids 35 to 269 are the mature chain.

FIG. 12 is the amino acid sequence of dennonecrotic toxin (SEQ ID NO:2).

FIG. 13 is the amino acid sequence of AmpG from *Bordetella pertussis* (SEQ ID NO:3).

FIG. 14 is the amino acid sequence of AmpG from *Escherichia coli* (SEQ ID NO:4).

DESCRIPTION OF THE PREFERRED EMBODIMENTS OF THE PRESENT INVENTION

Figure 1:
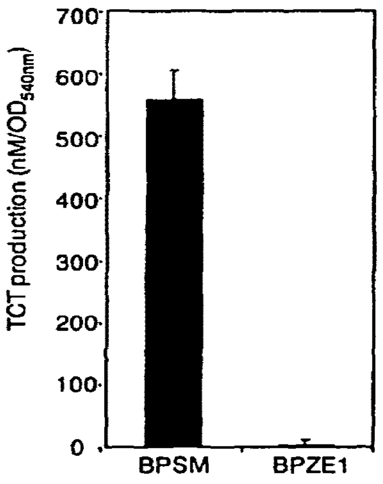
FIG. 1 is a bar graph illustrating the TCT present in culture supernatants of BPSM and BPZE expressed as means of nM/$OD_{540nm}$ (±standard error) of 3 separate cultures for each strain.

As used herein, the abbreviation "PTX" refers to pertussis toxin, which synthesizes and secretes an ADP-ribosylating toxin. PTX is composed of six polypeptides S1 to S5, the enzymatically active moiety is called S1. PTX has a 34 amino acid signal sequence, while the mature chain consists of amino acids 35 to 269. PTX is the major virulence factor expressed by *B. pertussis*. The A moiety of these toxins exhibit ADP-ribosyltransferase activity and the B portion mediates binding of the toxin to host cell receptors and the translocation of A to its site of action (57).

As used herein the abbreviation "DNT" refers to pertussis dermonecrotic toxin, which is a heat labile toxin that induces localized lesions in mice and other laboratory animals when it is injected intradermally. It is lethal to mice when it is injected in low doses intravenously (58 to 61). DNT is considered to be a virulence factor for the production of turbinate atrophy in porcine atrophic rhinitis (62, 63).

As used herein the abbreviation "TCT" refers to tracheal cytotoxin, which is a virulence factor synthesized by Bordetellae. TCT is a peptidoglycan fragment and has the ability to induce interleukin-1 production and nitric oxide synthase. It has the ability to cause stasis of cilia and has lethal effects on respiratory epithelial cells.

The term "mammal" encompasses any of various warm-blooded vertebrate animals of the class Mammalia, including humans, characterized by a covering of hair on the skin and, in the female, milk-producing mammary glands for nourishing the young.

The term "attenuated" means a weakened, less virulent *Bordetella* strain that is capable of stimulating an immune response and creating protective immunity, but does not cause any illness.

The terminology "rapid protective immunity" means that immunity against *Bordetella* is conferred in a short time after administration of the mutated *Bordetella* strain of the present invention. By "short time" means vaccinated and challenged one week later. More specifically, there is a quick expansion of existing pathogen-specific peripheral lymphocytes, CDS+ cytotoxic effectors (CTLs) and CD4+ helper cells. The CD4+ helper cells induce B cell maturation and antibody production. Thus, lymphocytes with the memory pool are poised to rapidly proliferate at the time of subsequent infection.

The term "*Bordetella* strain" encompasses strains from *Bordetella pertussis, Bordetella parapertussis* and *Bordetella bronchiseptica.*

The expression "*Bordetella* infection" means an infection caused by at least one of the three following strains: *Bordetella pertussis, Bordetella parapertussis* and *Bordetella bronchiseptica.*

By "child" is meant a person or a mammal between 6 months and 12 years of age.

By the term "newborn" is meant a person or a mammal that is between 1 day old and 24 weeks of age.

The term "treatment" as used herein is not restricted to curing a disease and removing its causes but particularly covered means to cure, alleviate. Remove or lessen the symptoms associated with the disease of interest, or prevent or reduce the possibility of contracting any disorder or malfunction of the host body.

The terms "protection" and "prevention" are used herein interchangeably and mean that an infection by *Bordetella* is impeded.

"Prophylaxis vaccine" means that this vaccine prevents *Bordetella* infection upon future exposure.

By "preferentially towards the Th1 pathway" is meant that the Th1 pathway is favored over the Th2 pathway.

The term "immunogenic composition" means that the composition can induce an immune response and is therefore antigenic. By "immune response" means any reaction by the immune system. These reactions include the alteration in the activity of an organism immune system in response to an antigen and may involve, for example, antibody production, induction of cell-mediated immunity, complement activation or development of immunological tolerance More specifically, the present invention provides at least a triple mutated *Bordetella* strain that can be used as an immunogenic composition or a vaccine. It will be appreciated that the at least triple mutated *Bordetella* strain contains a mutated ptx gene, a deleted or mutated dnt gene and a heterologous ampG gene. The heterologous ampG gene product reduces in large quantities the amount of tracheal cytotoxin that is produced.

The present invention is not limited to only the triple mutants described above. Other additional mutations can be undertaken such as adenylate cyclase (AC) deficient mutants (64), lipopolysaccharide (LPS) deficient mutants (65), filamentous hemagglutinin (FHA) (66) and any of the bvg-regulated components (67).

The starting strain which is mutated can be any *Bordetella* strain including *Bordetella pertussis, Bordetella parapertussis* and *Bordetella bronchiseptica*. In one aspect the starting strain used to obtain the mutated *Bordetella* strain is *B. pertussis*.

The construction of the mutated *Bordetella* strain starts with replacing the *Bordetella* ampG gene in the strain with a heterologous ampG gene. Any heterologous ampG gene can be used in the present invention. These include all those gram-negative bacteria that release very small amounts of peptidoglycan fragments into the medium per generation. Examples of gram-negative bacteria include, but are not limited to *Escherichia coli, Salmonella, Enterobacteriaceae, Pseudomonas, Moraxella, Helicobacter, Stenotrophomonas, Legionella* and the like.

By replacing the *Bordetella* ampG gene with a heterologous ampG gene, the amount of tracheal cytoxin (TCT) produced in the resulting strain expresses less than 1% residual TCT activity. In another embodiment, the amount of TCT toxin expressed by the resulting strain is between 0.6% to 1% residual TCT activity or 0.4% to 3% residual TCT activity or 0.3% to 5% residual TCT activity.

PTX is a major virulence factor responsible for the systemic effects of *B. pertussis* infections, as well as one of the major protective antigens. Due to its properties, the natural ptx gene is replaced by a mutated version so that the enzymatically active moiety S1 codes for an enzymatically inactive toxin, but the immunogenic properties of the pertussis toxin are not affected. This can be accomplished by replacing the arginine (Arg) at position 9 of the sequence with a lysine (Lys). Furthermore, a glutamic acid (Glu) at position 129 is replaced with a glycine (Gly).

Other mutations can also be made such as those described in U.S. Pat. No. 6,713,072, incorporated herein by reference, as well as any known or other mutations able to reduce the toxin activity to undetectable levels. Allelic exchange is first used to delete the ptx operon and then to insert the mutated version.

Finally, the dnt gene is then removed from the *Bordetella* strain by using allelic exchange. Besides the total removal, the enzymatic activity can also be inhibited by a point mutation. Since DNT is constituted by a receptor-binding domain in the N-terminal region and a catalytic domain in the C-terminal part, a point mutation in the dnt gene to replace Cys-1305 to Ala-1305 inhibits the enzyme activity of DNT (68). DNT has been identified as an important toxin in *Bordetella bronchiseptica* and displays lethal activity upon injection of minute quantities (26).

Besides allelic exchange to insert the mutated ptx gene and the inhibited or deleted dnt gene, the open reading frame of a gene can be interrupted by insertion of a genetic sequence or plasmid. This method is also contemplated in the present invention.

The triple mutated strain of the present invention is called a BPZE1 strain and has been deposited with the Collection Nationale de Cultures de Micrororganismes (CNCM) in Paris, France on Mar. 9, 2006 under the number CNCM 1-3585. The mutations introduced into BPZE1 result in drastic attenuation, but allow the bacteria to colonize and persist. Thus, in another embodiment the present invention provides BPZE1, which can induce mucosal immunity and systemic immunity when administered. In another aspect the BPZE1 is administered intranasally.

The mutated *Bordetella* strains of the present invention can be used in immunogenic compositions. Such immunogenic compositions are useful to raise an immune response, either an antibody response and or preferably a T cell response in mammals. Advantageously, the T cell response is such that it protects a mammal against *Bordetella* infection or against its consequences.

The mutated *Bordetella* strains of the present invention can be used as live strains or chemically or heat-killed strains in the vaccines or immunogenic compositions. In one aspect, the live strains are used for nasal administration, while the chemically—or heat killed strains can be used for systemic or mucosal administration.

The immunogenic composition may further comprise a pharmaceutically suitable excipient or carrier and/or vehicle, when used for systemic or local administration. The pharmaceutically acceptable vehicles include, but are not limited to, phosphate buffered saline solutions, distilled water, emulsions such as an oil/water emulsions, various types of wetting agents sterile solutions and the like.

The immunogenic composition of the invention can also comprise adjuvants, i.e., any substance or compound capable of promoting or increasing a T-cell mediated response, and particularly a $CD4^+$-mediated or $CD8^+$-mediated immune response against the active principle of the invention. Adjuvants such as muramyl peptides such as MDP. IL-12, aluminium phosphate, aluminium hydroxide, Alum and/or Montanide® can be used in the immunogenic compositions of the present invention.

It would be appreciated by the one skilled in the art that adjuvants and emulsions in the immunogenic compositions are used when chemically or heat treated mutated *Bordetella* strains are used in the vaccines or immunogenic compositions.

The immunogenic compositions of the invention further comprise at least one molecule having a prophylactic effect against a *Bordetella* infection or the detrimental effects of *Bordetella* infection, such as a nucleic acid, a protein, a polypeptide, a vector or a drug.

The immunogenic composition of the invention is used to elicit a T-cell immune response in a host in which the composition is administered. All immunogenic compositions described above can be injected in a host via different routes: subcutaneous (s.c.), intradermal (i.d.), intramuscular (i.m.) or intravenous (i.v.) injection, oral administration and intranasal administration or inhalation.

When formulated for subcutaneous injection, the immunogenic composition or vaccine of the invention preferably comprises between 10 and 100 μg of the *Bordetella* strain per injection dose, more preferably from 20 to 60 μg/dose, especially around 50 μg/dose, in a sole injection.

When formulated for intranasal administration, the *Bordetella* strain is administered at a dose of approximately $1\times10^3$ to $1\times10^6$ bacteria, depending on the weight and age of the mammal receiving it. In another aspect a dose of $1\times10^4$ to $5\times10^6$ can be used.

The mutated *Bordetella* strains of the present invention can be used as an attenuated vaccine to protect against future *Bordetella* infection. In this regard, an advantage of the present invention is that a single dose can be administered to mammals and the protection can last at least for a duration of longer than two months, particularly longer than six months. The vaccine of the present invention can be administered to newborns and protects against infection of whooping cough. This is especially crucial since the fatality rate from *Bordetella pertussis* infections is about 1.3% for infants younger than 1 month.

Moreover, the vaccines of the present invention can be used in adult mammals when there is an epidemic or in older adults over the age of 60, since their risk of complications maybe higher than that of older children or healthy adults.

The vaccines can be formulated with the physiological excipients set forth above in the same manner as in the immunogenic compositions. For instance, the pharmaceutically acceptable vehicles include, but are not limited to, phosphate buffered saline solutions, distilled water, emulsions such as an oil/water emulsions, various types of wetting agents sterile solutions and the like. Adjuvants such as muramyl peptides such as MDP. IL-12, aluminium phosphate, aluminium hydroxide, Alum and/or Montanide® can be used in the vaccines.

The vaccines of the present invention are able to induce high titers of serum IgG against FHA. The analysis of the antigen-specific cytokine patterns revealed that administration with the mutated attenuated *Bordetella* strains of the present invention favored a strong TH1 response.

The vaccines of the present invention provide high level of protection against a *Bordetella* infection i.e., a level of protection higher than 90%, particularly higher than 95%, more particularly higher than 99% (calculated 7 days after infection as detailed on example 9). The level of protection of the vaccine comprising the BPZE1 strain reaches more than 99.999% compared to non-vaccinated (naïve) mice, at least two months after vaccination.

The vaccines can be administered subcutaneous (s.c.), intradermal (i.d.), intramuscular (i.m.) or intravenous (i.v.) injection, oral administration and intranasal administration or inhalation. The administration of the vaccine is usually in a single dose. Alternatively, the administration of the vaccine of the invention is made a first time (initial vaccination), followed by at least one recall (subsequent administration), with the same strain, composition or vaccine, or with acellular vaccines, or a combination of both.

In one aspect, intranasal administration or inhalation of the vaccines is accomplished, which type of administration is low in costs and enables the colonization by the attenuated strains of the invention of the respiratory tract: the upper respiratory tract (nose and nasal passages, paranasal sinuses, and throat or pharynx) and/or the respiratory airways (voice box or larynx, trachea, bronchi, and bronchioles) and/or the lungs (respiratory bronchioles, alveolar ducts, alveolar sacs, and alveoli)

Intranasal administration is accomplished with an immunogenic composition or a vaccine under the form of liquid solution, suspension, emulsion, liposome, a cream, a gel or similar such multiphasic composition. Solutions and suspensions are administered as drops. Solutions can also be administered as a fine mist from a nasal spray bottle or from a nasal inhaler. Gels are dispensed in small syringes containing the required dosage for one application.

Inhalation is accomplished with an immunogenic composition or a vaccine under the form of solutions, suspensions, and powders; these formulations are administered via an aerosol or a dry powder inhaler. Compounded powders are administered with insufflators or puffers.

Use of the mutated *Bordetella* strains comprising at least a mutated ptx gene, a deleted or mutated dnt gene and a heterologous ampG gene for the preparation of a multivalent vaccine to treat respiratory diseases is yet another aspect of the present invention. In this regard, the attenuated mutated *Bordetella* strain described above, can be used as a heterologous expression platform to carry heterologous antigens to the respiratory mucosa. Thus, such respiratory pathogens such as *Neisseria, Pneumophila, yersinia, pseudomonas*, mycobacteria, influenza and the like can prevent infection using the BPZE1 as a carrier.

Use of the live attenuated mutated *Bordetella* strains described herein for the manufacture of a vaccine for the treatment or prevention of *Bordetella* infection is also encompassed by the present invention. In this regard, the vaccine can be used for the simultaneous treatment or prevention of an infection by *B. pertussis* and *B. parapertussis.*

Use of the vaccine to provide rapid protective immunity in case of a pertussis epidemic is also encompassed by the present invention.

Use of the vaccine to provide a rapid protective immunity, increasing over the at least next two months following vaccination is also encompassed by the present invention.

The vaccine or immunogenic composition is also provided in a kit. The kit comprises the vaccine or immunogenic composition and an information leaflet providing instructions for immunization.

The present invention also relates to a method for inducing T-cell mediated immune response and particularly a $CD4^+$-mediated immune response or a $CD8^+$-mediated immune response, comprising administering the live attenuated *Bordetella* strains of the invention in a non-human mammal or a human mammal.

A method of protecting a mammal against disease caused by infection by *Bordetella* comprising administering to said mammal in need of such treatment a mutated *Bordetella* strain comprising at least a mutated ptx gene, a deleted or mutated dnt gene, and a heterologous ampG gene is another embodiment of the present invention. This method encompasses treating or preventing infections against *Bordetella pertussis* and/or *Bordetella parapertussis*. In one aspect the BPZE1 strain is used in this method.

Also a method of providing a rapid protective immunity against a *Bordetella* infection comprising administering to said mammal in need of such treatment a mutated *Bordetella* strain comprising at least a mutated ptx gene, a deleted or mutated dnt gene, and a heterologous ampG gene is encompassed by the present invention. In one aspect the BPZE1 strain is used in this method.

Moreover, the mutated live attenuated *Bordetella* strains of the present invention induce mucosal immunity, as well as systemic immunity. Thus, in another aspect the invention also relates to a method of inducing mucosal and systemic immunity by administering to a mammal in need of such treatment the mutated live attenuated *Bordetella* strains of the present invention. In one aspect the BPZE1 strain is used in this method.

Besides its role in the prevention and/or treatment of *Bordetella* infection, the mutated strain of the invention may be used as vector, to bear at least one further heterologous nucleic acid sequence encoding a RNA (such as antisense RNA) or a protein of interest. This means that the mutated strain bears at least one further heterologous nucleic acid sequence in addition to the heterologous ampG gene. In one aspect, the protein encoded by this at least one further heterologous nucleic acid sequence is a protein for which the expression is desired in the respiratory tract. In another aspect, the protein of interest is an antigen, such as a viral, a bacterial or a tumoral antigen, against which an immune response is desired. Therefore, the mutated *Bordetella* strain bearing at least one further heterologous nucleic acid sequence may also be used as a vaccine. The definitions given above for administration of the vaccine or immunogenic composition also apply to a vaccine comprising mutated Bordetella strain bearing at least one further heterologous nucleic acid sequence. Examples of heterologous proteins are antigens of pathogens causing infections of or diseases associated with the respiratory track: poliomyelitis, influenza (influenzavirus from Orthomyxoviridae family) or antigens from pneumococcus (such as Streptococcus pneumoniae).

A number of embodiments of the invention have been described. Nevertheless, it will be understood that various modifications may be made without departing from the spirit and scope of the invention.

EXAMPLES

Materials and Methods

Example 1

Bordetella Strains and Growth Conditions

The B. pertussis strains used in this study were all derived from B. pertussis BPSM [13], and B. parapertussis is a streptomycin-resistant derivative of strain 12822 (kindly provided by Dr. N. Guiso, Lnstitut Pasteur Paris, France). All Bordetella strains were grown on Bordet-Gengou (BG) agar (Difco, Detroit, Mich.) supplemented with 1% glycerol, 20% defibrinated sheep blood, and 100 Lg/ml streptomycin. For cell adherence assays, exponentially growing B. pertussis was inoculated at an optical density of 0.15 at 600 nm in 2.5 ml modified Stainer-Scholte medium [14] containing 1 g/l heptakis(2,6-di-o-methyl) β-cyclodextrin (Sigma) and supplemented with 65 µCi/ml L-[$^{35}$S]methionine plus L-[$^{35}$S]cysteine (NEN, Boston, Mass.) and grown for 24 h at 37° C. The bacteria were then harvested by centrifugation, washed three times in phosphate-buffered saline (PBS) and resuspended in RPMI 1640 (Gibco, Grand Island, N.Y.) at the desired density.

Example 2

Construction of B. pertussis BPZE1

To construct B. pertussis BPZE1, the B. pertussis ampG gene was replaced by Escherichia coli ampG using allelic exchange. A PCR fragment named met and located at position 49,149 to 49.990 of the B. pertussis genome (http://www.sanger.ac.uk/Projects/B_pertussis/), upstream of the B. pertussis ampG gene, was amplified using oligonucleotides A: 5'-TATAAATCGATATTCCTGCTGGTTTCGTTCTC-3' (SEQ ID No:5) and B: 5'-TATAGCTAGCAAGT-TGGGAAACGACACCAC-3' (SEQ ID No:6), and B. pertussis BPSM [13] genomic DNA as a template. This 634 bp fragment was inserted into Topo PCRII (InVitrogen Life Technology, Groningen. The Netherlands) and then excised as a ClaI-NheI fragment and inserted into ClaI- and NheI-digested pBP23 [50], a suicide vector containing the E. coli ampG gene with flanking B. pertussis DNA of 618 bp (from position 50,474 to 51,092 of the B. pertussis genome) and 379 bp (from position 52,581 to 52.960 of the B. pertussis genome) at the 5' and 3' end of E. coli ampG, respectively. The resulting plasmid was transferred into E. coli SM10 [51], which was then conjugated with BPSM, and two successive homologous recombination events were selected as described [52]. Ten individual colonies were screened by PCR as follows. The colonies were suspended in 100 µl H$_2$O, heated for 20 min. at 95° C., and centrifuged for 5 min at 15,000×g. One µl of supernatants was then used as template for PCR using oligonucleotides A and C: 5'-TAAGAAGCAAAATAAGCCAGGCAIT-3' (SEQ ID No:7) to verify the presence of E. coli ampG and using oligonucleotides D: 5'-TATACCATGGCGCCGCTGCTG-GTGCTGGGC-3' (SEQ ID No:8) and E: 5'-TATATCTA-GACGCTGGCCGTAACCTTAGCA-3' (SEQ ID No:9) to verify the absence of B. pertussis ampG. One of the strains containing E. coli ampG and lacking B. pertussis ampG was then selected, and the entire ampG locus was sequenced. This strain was then used for further engineering.

The ptx genes were deleted from the chromosome of this strain as described [21] and then replaced by mutated ptx coding inactive PTX. The EcoRI fragment containing the mutated ptx locus from pPT-RE [16] was inserted into the EcoRI site of pJQ200mp18rpsl [53]. The resulting plasmid was integrated into the B. pertussis chromosome at the ptx locus by homologous recombination after conjugation via E. coli SM10. The ptx locus in the chromosome of the resulting B. pertussis strain was sequenced to confirm the presence of the desired mutations. Toxin production was analyzed by immunoblotting using a mix of monoclonal antibodies IB7 [54] specific for subunit S1, and 11E6 [55] specific for subunits S2 and S3 of PTX.

Finally, the dnt gene was deleted from the resulting B. pertussis strain as the dnt flanking regions were amplified by PCR using BPSM genomic DNA as a template and oligonucleotides F: 5'-TATAGAATTCGCTCGGTCGCTGGT-CAAGG-3' (SEQ ID No:10) and G: 5'-TATATCTAGAG-CAATGCCGATTCATCTTTA-3' (SEQ ID No:11) for the dnt upstream region, and H: 5'-TATATCTAGAGCGGCCTT TATTGCTITTCC-3' (SEQ ID No:12) and I: 5'-TATAAAGCTTCTCATGCACGCCG GCTTCTC-3' (SEQ ID No:13) for the dnt downstream region, as primers. The resulting 799-bp and 712-bp DNA fragments were digested with EcoRI/XbaI and XbaI/HindIII, respectively, and linked together using the Fast Link kit (Epicentre Biotechnologies, Madison, Wis.). The ligated fragment was amplified by PCR using oligonucleotides F and 1, and the 1505-bp PCR fragment was then inserted into pCR2.1-Topo (Invitrogen), re-isolated from the resulting plasmid as an EcoRI fragment and inserted into the unique EcoRI site of pJQmp200 rpsL18. The resulting plasmid was introduced into B. pertussis by conjugation via E. coli SM10, Successful deletion of the dnt gene by allelic exchange was verified by Southern blot analysis on PvuII-digested B. pertussis genomic DNA using the PCR fragment corresponding to the dnt upstream region as a probe. The probe was labeled with digoxigenin (DIG) using the DIG Easy Hyb labeling kit (Roche, Meylan, France). The sizes of the hybridizing bands were determined from the migration distance of the Dig-labeled DNA molecular marker III (Roche). The dnt locus of this final strain, named BPZE1 was sequenced.

Example 3

Analysis of TCT Production

For sensitive quantitation of TCT production, culture supernatants of B. pertussis grown to logarithmic phase were collected, subjected to solid phase extraction [15] and derivatized with phenylisothiocyanate (PITC, Pierce). The resulting phenylthiocarbamyl (PTC) derivatives were separated by reversed-phase HPLC using a C8 column (Perkin Elmer) and detected at 254 nm. The amount of *B. pertussis* PTC-TCT in each sample was determined by comparing the peak area and elution time with an identically processed TCT standard.

Example 4

Cell-Adherence Assay

To analyze adherence properties of the *B. pertussis* strains, their attachment rates to the human pulmonary epithelial cell line A549 (ATCC n° CCL-185) and the murine macrophage cell line J774 (ATCC n° TIB-67) were measured as previously described [16].

Example 5

Transmission Electron Microscopy

The single droplet-negative staining procedure was used as described previously [17] with the following modifications. 20 μl of a suspension at approximately $10^9$ bacteria/ml were absorbed for 2 min. onto form formvard carbon-coated nickel grids (400 mesh; Electron Microscopy Sciences EMS, Washington, Pa.). After 30 seconds air-drying the grids were stained for 2 minutes with 20 μl of 2% phosphotungstic acid (pH7; EMS) and examined after air-drying under a transmission electron microscope (Hitachi 7500, Japan) at 60 kvolts and high resolution.

Example 6

Intranasal Infection and Vaccination 3-week and 8-week old female Balb/C were kept under specific pathogen-free conditions, and all experiments were carried out under the guidelines of the Institut Pasteur de Lille animal study board. Mice were intranasally infected with approximately $4\times10^6$ bacteria in 20 μl PBS, and kinetics of CFU in the lungs were measured as previously described [18]. For vaccination with aPV (Tetravac; Aventis-Pasteur, France), mice were immunized intraperitoneally (i.p.) with 20% of the human dose and boosted one month later using the same dose.

Example 7

Antibody Determination

Sera were collected, and antibody titers were estimated by enzyme-linked immunosorbent assays (ELISA) as previously described [18].

Example 8

Cytokine Assays

Spleen cells from individual mice were tested at different time points after immunization for in vitro cytokine production in response to heat-killed *B. pertussis* BPSM ($10^6$ cells/ml), 5.0 μg/ml PTX (purified from *B. pertussis* BPGR4 [19] as previously described [20] and heat-inactivated at 80° C. for 20 min). 5.0 μg filamentous hemagglutinin (FHA, purified from *B. pertussis* BPRA [21] as previously described [22]), 5 μg/ml concanavalin A (Sigma Chemical Co., St. Louis, Mo.) or medium alone as control. Supernatants were removed from triplicate cultures after 72 h incubation at 37° C. and 5% $CO_2$, and IFN-γ and IL-5 concentrations were determined by immunoassays (BD OptEIA set, Pharmingen).

Example 9

Intranasal Infection and Vaccination: Challenge at 1, 2, 3 and 4 Weeks

An infant (3 weeks-old) mouse model [29] was used to compare the efficiency of vaccination with BPZE1 with the one of vaccination with acellular pertussis vaccine (aPv). Female Balb/C mice were intranasally infected with approximately $1\times10^6$ BPZE1 strain in 20 μl PBS. For vaccination with aPv (Tetravac; Aventis-Pasteur, France), mice were immunized intraperitoneally with 20% of the human dose. One, two, three or four weeks after vaccination with BPZE1 or aPv, mice were intranasally challenged with virulent *B. pertussis* BPSM/bctA-lacZ strain [53]. This strain is a BPSM-derivative gentamycin-resistant which allows the discrimination with BPZE1 (gentamycin-sensitive) on Bordet-Gengou agar plates containing 10 μg/ml of gentamycin and 100 μg/ml of streptomycin (Bogs). Control group corresponds to naive mice challenged with BPSM/bctA-lacZ. One week after challenge infection, lungs were aseptically removed, homogenized and plates on BGgs for CFU determination as previously described [18].

Mice were vaccinated with BPZE1 or aPv and challenged with virulent *B. pertussis* one, two, three or four weeks after vaccination. Lung CFUs counts were determined 3 hours or 7 days later. Results are expressed as mean (±standard error) CFUs from three to five mice per group. Levels of protection are calculated for each challenge infection as mean percentages of CFUs of each group relative of the average of CFUs in non-immunized group, 7 days after challenge infection (Tables 2 to 5).

Example 10

Statistical Analysis

The results were analyzed using the unpaired Student's t test and the Kruskal-Wallis test followed by the Dunn's post-test (GraphPad Prism program) when appropriate. Differences were considered significant at $P\leq0.05$.

Results

Construction of *B. pertussis* BPZE1

Three virulence factors were genetically targeted: tracheal cytotoxin (TCT), pertussis toxin (PTX) and dermonecrotic toxin (DNT).

TCT is responsible for the destruction of ciliated cells in the trachea of infected hosts [24, 25] and may thus be involved in the cough syndrome. TCT is a breakdown product of peptidoglycan in the cell wall of Gram-negative bacteria, which generally internalize it into the cytosol by the AmpG transporter protein to be re-utilized during cell wall biosynthesis. *B. pertussis* AmpG is inefficient in the internalization of peptidoglycan breakdown products. We therefore replaced the *B. pertussis* ampG gene by *E. coli* ampG. The resulting strain expressed less than 1% residual TCT activity (FIG. 1).

Figure 2:
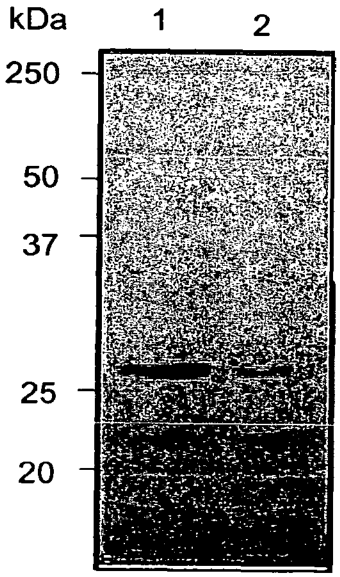
FIG. 2 is an immunoblot analysis of PTX production in the culture supernatants of BPSM (lane 1) and BPZE1 (lane 2). The sizes of the Mr markers are expressed in kDa and given in the left margin.

PTX is a major virulence factor responsible for the systemic effects of *B. pertussis* infections and is composed of an enzymatically active moiety, called S1, and a moiety responsible for binding to target cell receptors (for review, see 26). However, it is also one of the major protective antigens, which has prompted us to replace the natural ptx genes by a mutated version coding for an enzymatically inactive toxin. This was achieved by replacing Arg-9 by Lys and Glu-129 by Gly in S1, two key residues involved in substrate binding and catalysis, respectively. Allelic exchange was used to first delete the ptx operon, and then to insert the mutated version. The presence of the relevant toxin analogues in the *B. pertussis* culture supernatants was evaluated by immunoblot analysis (FIG. 2).

Figure 3:
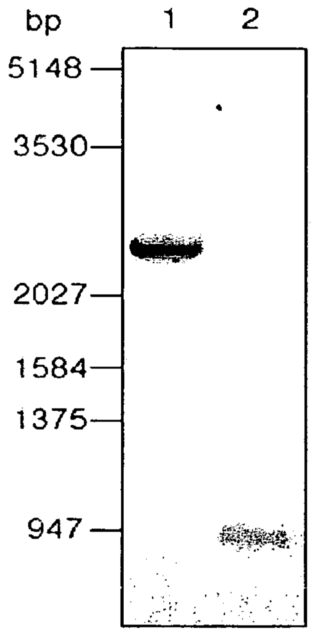
FIG. 3 is a Southern-blot analysis of the dnt locus in BPSM (lane 1) and BPZE (lane 2). The lengths of the size markers are indicated in base pairs (bp) are shown in the left margin.

Finally, allelic exchange was used to remove the dnt gene (FIG. 3). Although the role of DNT in the virulence of *B. pertussis* is not certain, it has been identified as an important toxin in the closely related species *Bordetella bronchiseptica* and displays lethal activity upon injection of minute quantities (for review, see 26).

In Vitro Characterization of *B. pertussis* BPZE1

Figure 4:
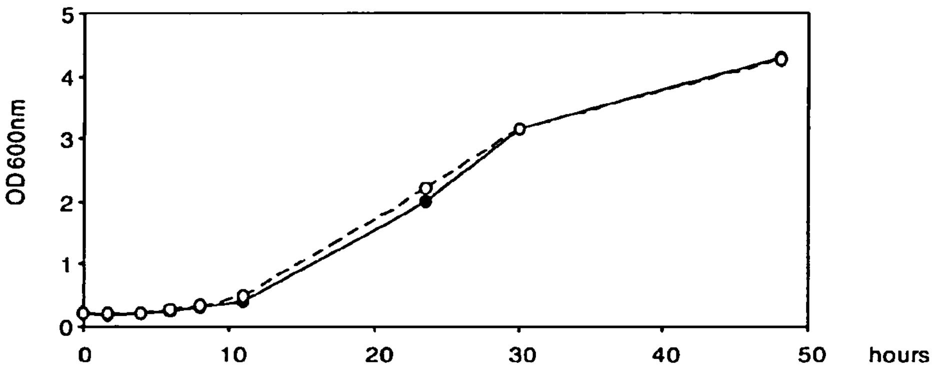
FIG. 4 is a graph illustrating the growth rates of BPSM (black line) and BPZE1 (dotted line) in liquid culture.
Figure 5:
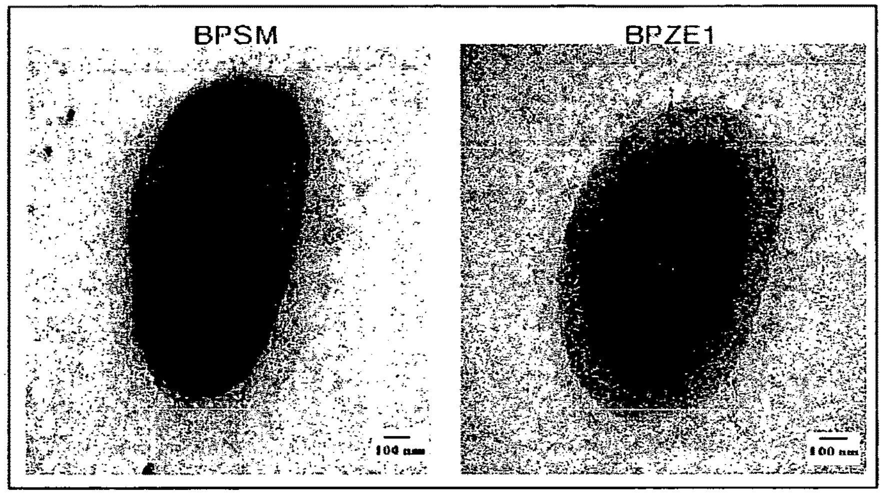
FIG. 5 are electron micrographs representative of BPSM (left) and BPZE1 (right) grown in liquid medium for 24 h.

Since some of the genetic alterations in BPZE1 may potentially affect the bacterial cell wall synthesis, the size and shape, as well as the in vitro growth rate of BPZE1 was compared with those of the parental strain BPSM. The growth rate of BPZE1 did not differ from that of BPSM (FIG. 4), and no difference in bacterial shape or size was detected between BPZE1 and BPSM, as evidenced by electron microscopy analysis (FIG. 5). However, the cell wall of BPZE1 appeared to be consistently somewhat thinner than that of BPSM.

Figure 6:
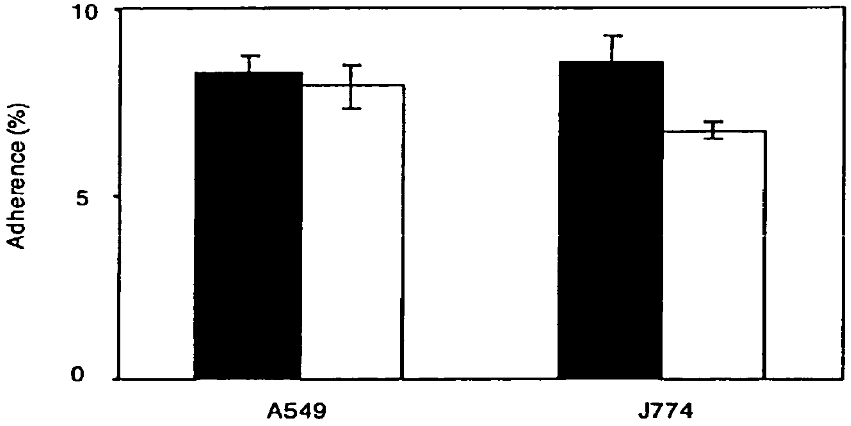
FIG. 6 is a graph illustrating the in vitro adherence of BPSM (black columns) and BPZE1 (white columns) to human pulmonary epithelial A549 cells (left) and murine macrophage-like J774 cells (right). The results are expressed as means of percentages of binding bacterial relative to the bacteria present in the inoculum from three different experiments.

To determine whether the absence or alterations of any of the targeted toxins in BPZE1 affects adherence properties of *B. pertussis*, the attachment rates of BPZE1 was compared with those of BPSM, using the human pulmonary epithelial cell line A549 and the murine macrophage cell line J774, as two cellular models often used to study the adherence of *B. pertussis*. No significant difference in the adherence capacities to either cell line was observed between the two strains (FIG. 6).

Attenuation of *B. pertussis* BPZE

Figure 7:
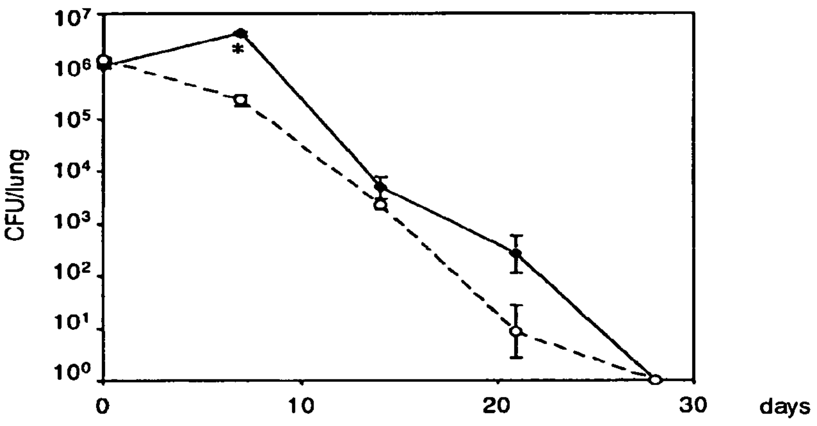
FIG. 7 is a graph illustrating lung colonization by BPSM (black lines) and BPZE1 (dotted lines) of adult mice infected intranasally with 106 CFU of BPZE1 or BPSM. The results are expressed as mean (±standard error) CFUs from three to four mice per group and are representative of two separate experiments. P=0.004.
Figure 8:
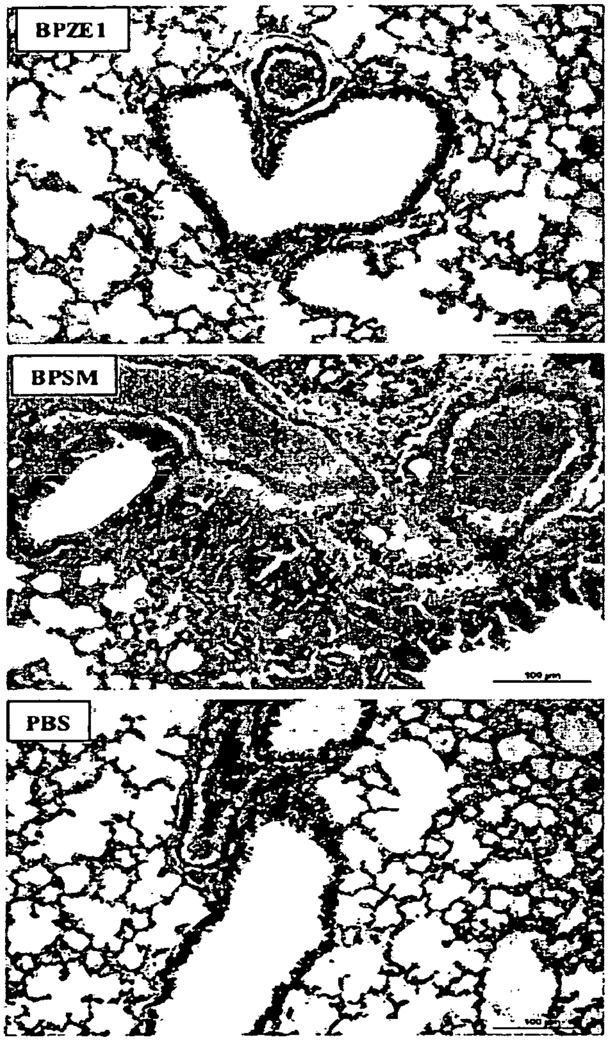
FIG. 8 are photographs of a histological analysis of lungs from BPZE1 (upper panel) or BPSM-infected (middle panel) adult mice compared to controls given PBS (lower panel). One week after infection, the lungs were aseptically removed and fixed in formaldehyde. Sections were stained with hematoxylin and eosin and examined by light microscopy.

To determine whether the mutations introduced into *B. pertussis* BPZE1 have resulted in attenuation, yet allow the organism to colonize the respiratory tract, Balb/C mice were intranasally infected with BPZE1 or BPSM, and colonization was followed over time. BPZE1 was able to colonize and persist in the lungs of mice as long as BPSM (FIG. 7). However, the peak of multiplication seen 7 days after infection with BPSM was consistently lacking in mice infected with BPZE1. Studies done with strains mutated in individual toxin genes indicated that this is due to the mutations in the ptx locus (data not shown). When the lungs were examined for histopathological changes and inflammatory infiltration, infection with BPSM was found to induce strong peri-bronchiovascular infiltrates and inflammatory cell recruitment 7 days after infection, associated with a strong hypertrophy of the bronchiolar epithelial cells (FIG. 8). In contrast, no such changes were seen in BPZE1-infected animals, and the histology of the BPZE1-infected mice was similar to that of the control mice that had received PBS instead of the bacteria. The BPSM-infection induced inflammation lasted for at least two months (data not shown). These results indicate that the mutations introduced into BPZE1 have resulted in drastic attenuation, but allow the bacteria to colonize and persist in the lungs.

Protection Against *B. pertussis* Challenge after Intranasal Vaccination of Adult Mice with BPZE1

Figure 9:
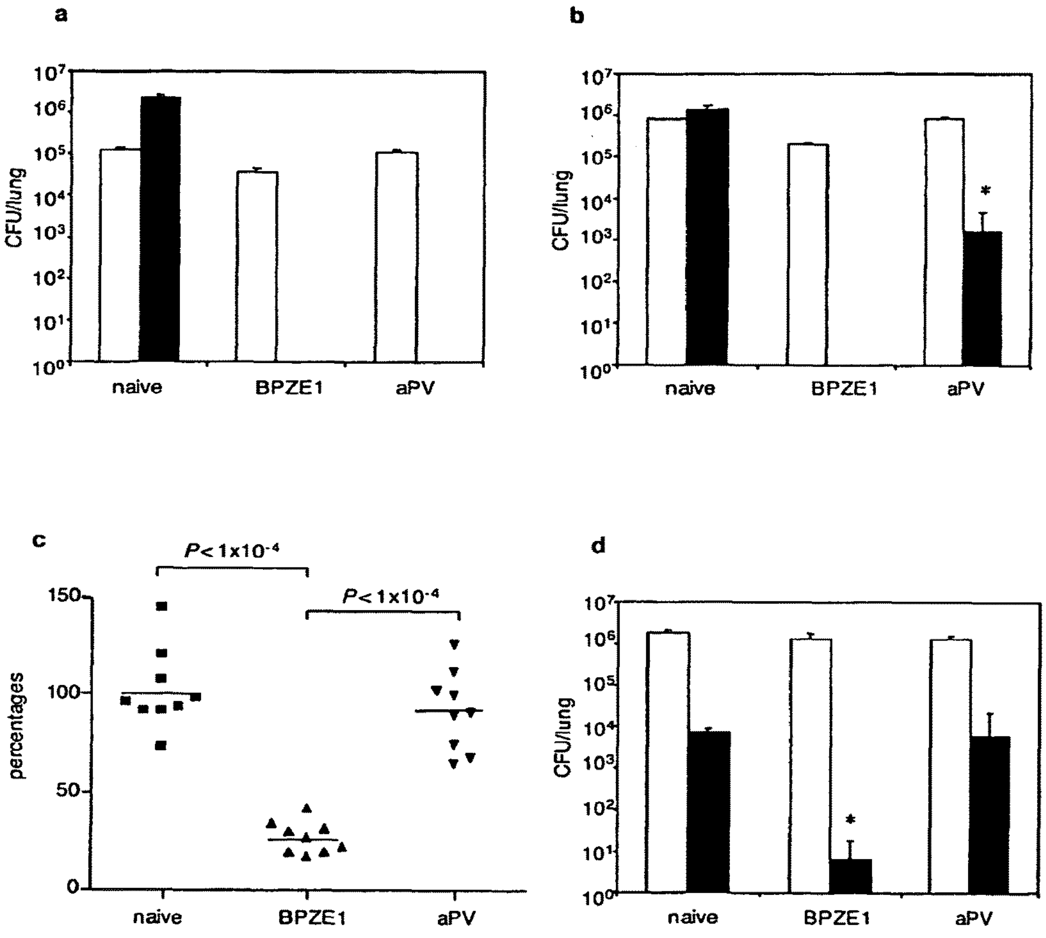
FIG. 9 are graphs illustrating the protection against *B. pertussis* in (a) adult and (b) infant mice or *B. parapertussis* in infant mice (d). Mice immunized with BPZE1, aPV or PBS (naive) were challenged with BPSM (a and b) or *B. parapertussis* (d), and lung CFU counts were determined 3 h (white bars) or 7 days (black bars) later. Results are expressed as mean (±standard error) CFUs from 3-4 mice per group and are representative of two separate experiments. (b,*, P=0.009; d,*, P=0.007) (c) CFU counts 3 h after BPSM challenge in adult mice vaccinated with BPZE1 or aPV, compared to controls. Results obtained from 3 separate experiments are expressed as percentages of CFUs of each mouse relative of the average of CFUs in non-immunized group from the same experiment.

To evaluate the protection offered by BPZE1, the effect of a single intranasal administration of this strain to 8-weeks old Balb/C mice on the subsequent colonization by the wild type challenge strain BPSM was compared with that of two i. p. immunizations with ⅕ of a human dose of aPV. This aPV immunization protocol has been described as the best to correlate with pertussis vaccine efficacy in human clinical trials 127, 281. As shown by the total clearance of bacterial colony counts in the lungs seven days after challenge infection, a single intranasal administration of BPZE1 and two i.p. immunizations with aPV provided similar levels of protection (FIG. 9*a*). High bacterial loads were found in the control mice that had received two injections of PBS instead of the vaccine.

Protection Against *B. pertussis* Challenge after Intranasal Vaccination of Infant Mice with BPZE1

Since the principal targets of novel pertussis vaccines are young infants, that are not protected with the currently available vaccines, an infant (3 weeks-old) mouse model 1291 was developed and used to compare the efficiency of vaccination with BPZE1 with that of vaccination with aPV. A single nasal administration of BPZE1 fully protected infant mice against challenge infection (FIG. 9*b*), as complete bacterial clearance was observed in the lungs one week after challenge. In contrast, substantial numbers of bacteria remained in the aPV-vaccinated animals one week after challenge infection. The difference in bacterial load between the BPZE1-vaccinated and the aPV-vaccinated mice was statistically significant, indicating that in the infant mouse model a single intranasal administration with BPZE1 provides better protection than two systemic administrations of aPV.

In addition, a strong reduction in the bacterial load of the challenge strain 3 hours after administration when the mice had been immunized with BPZE1 was consistently observed compared to the aPV-immunized animals (FIG. 9*c*), indicating that vaccination with BPZE1 reduces the susceptibility to infection by the challenge strain. This effect was seen in both 8-weeks old and in infant mice. In contrast, aPV had no effect on the bacterial counts 3 hours after infection, when compared to the control mice.

Protection Against *B. parapertussis* Challenge after Intranasal Vaccination with BPZE1

There is increasing concern about *B. parapertussis* infection in children, especially in immunized populations [30, 31]. *B. parapertussis* causes a milder pertussis-like syndrome, the frequency of which is probably largely underestimated. Furthermore, the incidence of *B. parapertussis* infections has been increasing over the last decades, possibly due to the fact that pertussis vaccines are known to have very low or no protective efficacy against *B. parapertussis* (32, 331. In contrast, infection by *B. pertussis* has recently been reported to protect against *B. parapertussis* infection [34]. BPZE1 was also assessed for protection against *B. parapertussis* using the infant mouse model. Whereas two administrations of aPV did not provide any protection against *B. parapertussis*, as previously reported, a single intranasal administration of BPZE1 provided strong protection, as measured by the low numbers of *B. parapertussis* counts in the lungs of the vaccinated mice 1 week after challenge (FIG. 9*d*).

Immune Responses Induced by BPZE1 Vaccination

Figure 10:
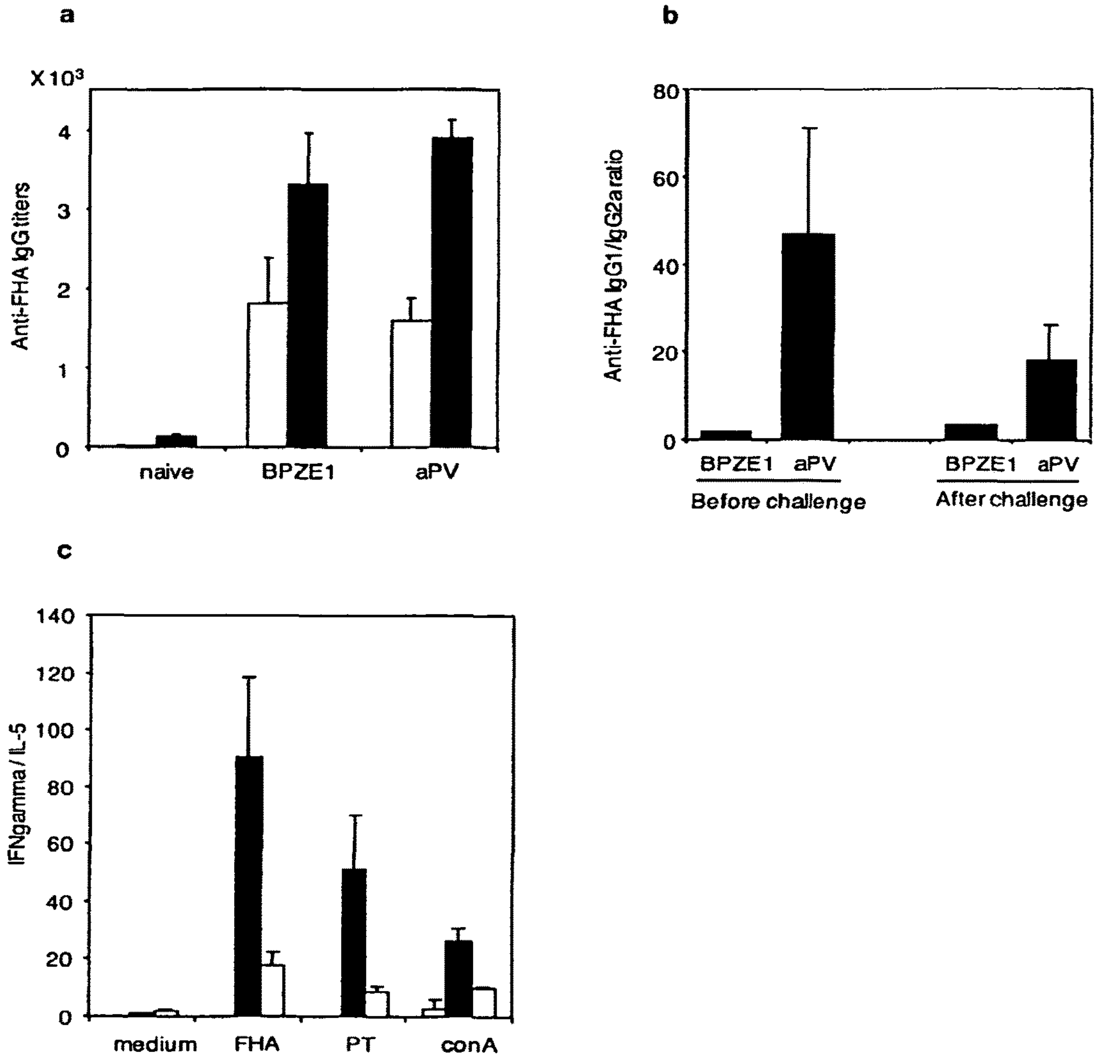
FIG. 10 are bar graphs illustrating the immune responses induced by BPZE1 or aPV immunization. (a) Anti-FHA lgG(H+1) titers and (b) lgG1/IgG2a ratios before (white bars) or 1 week after BPSM challenge (black bars) in BPZE1 or aPV immunized mice, compared to controls. (c) IFN-y to IL-5 ratios produced by FHA-, PTX- or ConA-stimulated splenocytes from mice vaccinated 2 months before with BPZE1 (black bars) or aPV (white bars), compared to controls (gray bars). Antibodies and cytokines were measured in individual mice, and the results are expressed as mean values (±standard error) for 4 mice per group tested in triplicate.

Although the mechanisms of protective immunity against *B. pertussis* infection are not yet completely understood, clear evidence of a role for both B cells and IFN-γ has been demonstrated in mice [28]. Vaccination with either one nasal dose of BPZE1 or two i. p. administrations of aPV induced high titers of serum IgG against FHA, a major surface antigen of *B. pertussis* [35], also present in aPV (FIG. 10*a*). Following *B. pertussis* challenge, positive anamnestic responses were measured in BPZE1- and in aPV-vaccinated animals, as indicated by an increase in anti-FHA IgG titers, compared to primary responses before *B. pertussis* infection.

Examination of the anti-FHA IgG1/IgG2a ratios showed that these ratios were higher after aPV administration, characteristic of a Th2 type response, than after BPZE1 vaccination (FIG. 10*b*). Although the anti-FHA-IgG/IgG2a decreased after challenge in the aPV vaccinated mice, it remained still substantially higher than in the BPZE1-vaccinated animals after *B. pertussis* challenge.

Analysis of *B. pertussis* antigen-specific cytokine patterns induced by BPZE1 or aPV vaccination confirmed that BPZE1 administration favors a stronger Th1 type response than aPV vaccination. This was revealed by the fact that the ratios of IFN-γ over IL-5 produced by splenocytes stimulated with FHA or PT, or with the polyclonal activator ConA were significantly higher in BPZE1 vaccinated mice than in aPV vaccinated mice (FIG. 10*c*).

Protective Immunity of BPZE1 Over Time (from 1 Week to 4 Weeks)

As shown in Tables 1 to 5 below, whereas administration of aPv provided limited protection (reduction of 75% of bacterial load compared to non-vaccinated mice at 1 week) against *B. pertussis*, a single intranasal administration of BPZE1 already provided high level of protection (reduction of 97.64% of bacterial load) against a *B. pertussis* challenge infection performed one week after vaccination. If challenge infection occurred two weeks after vaccination, the level of protection induced by BPZE1 reached more than 99.999% compared to non-vaccinated mice and is significantly superior to the protection induced by aPv vaccine (approximately 92% compared to non-vaccinated mice). Therefore, vaccine efficacy of BPZE1 against *B. pertussis* challenge is already significant one week after vaccination and is increasing over the at least next two months.

TABLE 1

Kinetics of vaccines efficacy against *B. pertussis* challenge in infant mice.

| Time between vaccination and challenge | Time between lungs recovery and challenge | Log10 cfu/lungs of mice: Naive | aPv-vaccinated | BPZE1-vaccinated |
|---|---|---|---|---|
| 1 week | 3 hours | 5.71 ± 0.03 | 5.8 ± 0.07 | 5.74 ± 0.01 |
| | 7 days | 6.71 ± 0.06 | 5.97 ± 0.20 | 4.86 ± 0.35 |
| 2 weeks | 3 hours | 5.77 ± 0.10 | 5.60 ± 0.02 | 5.49 ± 0.05 |
| | 7 days | 6.49 ± 0.08 | 5.31 ± 0.16 | 3.22 ± 0.33 |
| 3 weeks | 3 hours | 6.03 ± 0.11 | 5.88 ± 0.04 | 5.33 ± 0.08 |
| | 7 days | 6.58 ± 0.09 | 5.62 ± 0.11 | 3.14 ± 0.38 |
| 4 weeks | 3 hours | 6.31 ± 0.01 | 6.15 ± 0.02 | 5.83 ± 0.05 |
| | 7 days | 6.36 ± 0.04 | 5.21 ± 0.11 | 1.83 ± 0.46 |

TABLE 2

Level of protection of aPv-vaccinated and BPZE1-vaccinated mice as compared to non-vaccinated mice at week 1.

| Non vaccinated mice | Number of bacteria in lungs | Mean number of bacteria |
|---|---|---|
| Non-vaccinated 1 | $4.7 \times 10^6$ | $5.36 \cdot 10^6$ |
| Non-vaccinated 2 | $3.8 \times 10^6$ | |
| Non-vaccinated 3 | $8.2 \times 10^6$ | |
| Non-vaccinated 4 | $4.1 \times 10^6$ | |
| Non-vaccinated 5 | $6 \times 10^6$ | |

TABLE 2-continued

Level of protection of aPv-vaccinated and BPZE1-vaccinated mice as compared to non-vaccinated mice at week 1.

| | Number of bacteria in lungs | Percentage of remaining bacteria [(1)] | Mean percentage of remaining bacteria | Level of protection |
|---|---|---|---|---|
| **aPv-vaccinated mice** | | | | |
| aPv1 | $1.95 \times 10^6$ | 36.38 | 25% | 75% |
| aPv2 | $2.9 \times 10^6$ | 54.1 | | |
| aPv3 | $2.9 \times 10^5$ | 5.41 | | |
| aPv4 | $3.6 \times 10^5$ | 6.72 | | |
| aPv5 | $1.2 \times 10^6$ | 22.39 | | |
| **BPZE1-vaccinated mice** | | | | |
| BPZE1-1 | $3.2 \times 10^5$ | 5.97 | 2.36% | 97.64% |
| BPZE1-2 | $2 \times 10^4$ | 0.004 | | |
| BPZE1-3 | $6 \times 10^4$ | 1.12 | | |

(1) Percentage of remaining bacteria = number of bacteria for each particular mouse/mean number of bacteria of all non-vaccinated mice

TABLE 3

Level of protection of aPv-vaccinated and BPZE1-vaccinated mice as compared to non-vaccinated mice at week 2.

| Non vaccinated mice | Number of bacteria in lungs | Mean number of bacteria |
|---|---|---|
| Non-vaccinated 1 | $5 \times 10^6$ | $3.34 \times 10^6$ |
| Non-vaccinated 2 | $3.6 \times 10^6$ | |
| Non-vaccinated 3 | $1.7 \times 10^6$ | |
| Non-vaccinated 4 | $2.4 \times 10^6$ | |
| Non-vaccinated 5 | $4 \times 10^6$ | |

| | Number of bacteria in lungs | Percentage of remaining bacteria [(1)] | Mean percentage of remaining bacteria | Level of protection |
|---|---|---|---|---|
| **aPv-vaccinated mice** | | | | |
| aPv1 | $9.5 \times 10^4$ | 2.84 | 8.11% | 91.89% |
| aPv2 | $2.9 \times 10^5$ | 8.68 | | |
| aPv3 | $1 \times 10^5$ | 2.99 | | |
| aPv4 | $6.8 \times 10^5$ | 20.36 | | |
| aPv5 | $1.9 \times 10^5$ | 5.69 | | |
| **BPZE1-vaccinated mice** | | | | |
| BPZE1-1 | $9.5 \times 10^3$ | $2.8 \times 10^{-3}$ | $1.03 \times 10^{-3}$% | 99.999% |
| BPZE1-2 | 450 | $1.35 \times 10^{-4}$ | | |
| BPZE1-3 | 3500 | $1.05 \times 10^{-3}$ | | |
| BPZE1-4 | 500 | $1.5 \times 10^{-4}$ | | |

(1) Percentage of remaining bacteria = number of bacteria for each particular mouse/mean number of bacteria of all non-vaccinated mice

TABLE 4

Level of protection of aPv-vaccinated and BPZE1-vaccinated mice as compared to non-vaccinated mice at week 3.

| Non vaccinated mice | Number of bacteria in lungs | Mean number of bacteria |
|---|---|---|
| Non-vaccinated 1 | $1.8 \times 10^6$ | $4.04 \times 10^6$ |
| Non-vaccinated 2 | $5.75 \times 10^6$ | |
| Non-vaccinated 3 | $4.7 \times 10^6$ | |
| Non-vaccinated 4 | $3.2 \times 10^6$ | |
| Non-vaccinated 5 | $4.75 \times 10^6$ | |

TABLE 4-continued

Level of protection of aPv-vaccinated and BPZE1-vaccinated mice as compared to non-vaccinated mice at week 3.

| | Number of bacteria in lungs | Percentage of remaining bacteria [(1)] | Mean percentage of remaining bacteria | Level of protection |
|---|---|---|---|---|
| aPv-vaccinated mice | | | | |
| aPv1 | $1.99 \times 10^5$ | 4.94 | 11.26% | 88.74% |
| aPv2 | $6 \times 10^5$ | 14.85 | | |
| aPv3 | $6 \times 10^5$ | 14.85 | | |
| aPv4 | $4.2 \times 10^5$ | 10.40 | | |
| BPZE1-vaccinated mice | | | | |
| BPZE1-1 | 3640 | $9.01 \times 10^{-4}$ | $8.65 \times 10^{-4}$% | 99.999% |
| BPZE1-2 | 9720 | $2.4 \times 10^{-3}$ | | |
| BPZE1-3 | 300 | $7.43 \times 10^{-5}$ | | |
| BPZE1-4 | 340 | $8.42 \times 10^{-5}$ | | |

[(1)] Percentage of remaining bacteria = number of bacteria for each particular mouse/mean number of bacteria of all non-vaccinated mice

TABLE 5

Level of protection of aPv-vaccinated and BPZE1-vaccinated mice as compared to non-vaccinated mice at week 4.

| Non vaccinated mice | Number of bacteria in lungs | Mean number of bacteria |
|---|---|---|
| Non-vaccinated 1 | $2.1 \times 10^6$ | $2.36 \times 10^6$ |
| Non-vaccinated 2 | $2.2 \times 10^6$ | |
| Non-vaccinated 3 | $3.1 \times 10^6$ | |
| Non-vaccinated 4 | $2.6 \times 10^6$ | |
| Non-vaccinated 5 | $1.8 \times 10^6$ | |

| | Number of bacteria in lungs | Percentage of remaining bacteria [(1)] | Mean percentage of remaining bacteria | Level of protection |
|---|---|---|---|---|
| aPv-vaccinated mice | | | | |
| aPv1 | $2.52 \times 10^5$ | 10.68 | 7.76% | 92.24% |
| aPv2 | $3.28 \times 10^5$ | 13.90 | | |
| aPv3 | $1.04 \times 10^5$ | 4.41 | | |
| aPv4 | $8.4 \times 10^5$ | 3.56 | | |
| aPv5 | $1.48 \times 10^5$ | 6.27 | | |
| BPZE1-vaccinated mice | | | | |
| BPZE1-1 | 190 | $8.05 \times 10^{-5}$ | $7.13 \times 10^{-5}$% | 99.999% |
| BPZE1-2 | 0 | 0 | | |
| BPZE1-3 | 110 | $4.66 \times 10^{-5}$ | | |
| BPZE1-4 | 320 | $1.36 \times 10^{-4}$ | | |
| BPZE1-5 | 220 | $9.32 \times 10^{-5}$ | | |

[(1)] Percentage of remaining bacteria = number of bacteria for each particular mouse/mean number of bacteria of all non-vaccinated mice

Discussion

Pertussis is the first infectious disease whose incidence is increasing in countries with high vaccine coverage. This paradoxical situation is most likely linked to the epidemiological changes observed since the massive introduction of highly efficacious vaccines. In contrast to the pre-vaccination era. cases of adolescent and adult pertussis are now increasingly more frequent. Although generally not life-threatening in that age group, *B. pertussis*-infected adults are an important reservoir for infection of the very young children, too young to be protected by vaccination. Early vaccination, possibly at birth, would therefore be highly desirable, but is hampered by the immaturity of the immune system of neonates and infants. However, the fact that natural *B. pertussis* infection, even very early in life, is able to induce a strong Th1 response in infants [12] prompted us to develop a live attenuated *B. pertussis* vaccine strain to be given by the nasal route as an alternative over the currently available vaccines.

Based on experimental infections of primates, Huang et al. had already in 1962 come to the conclusion that ultimate protection against whooping cough probably best follows a live *B. pertussis* inoculation [36]. In veterinary medicine, attenuated *Bordetella* strains have been used to vaccinate against bordetellosis in dogs and piglets. A live attenuated *Bordetella bronchiseptica* strain has been shown to provide strong protection against kennel cough in dogs [37 ] after nasal administration. This protection was seen as early as 48 h after vaccination. Intranasal vaccination with live attenuated *B. bronchiseptica* has also been shown to protect against atrophic rhinitis in two-days old piglets [38], indicating that in a live attenuated form *Bordetella* vaccines can be highly active in new-born animals.

Previous attempts to genetically attenuate *B. pertussis* as a live vaccine candidate have met with rather limited success. Based on a strategy used for the successful attenuation of *Salmonella* vaccine strains [39], Roberts et al. have deleted the aroA gene of *B. pertussis* [40]. The aroA mutant was indeed highly attenuated, but had also lost its capacity to colonize the respiratory tract of the intranasally vaccinated animals and induced protective immunity only after repeated administrations of high doses. We took advantage of the knowledge on the molecular mechanisms of *B. pertussis* virulence and developed the highly attenuated strain BPZE1. This strain contains genetic alterations leading to the absence or inactivation of three major toxins, PTX, TCT and DNT. In contrast to the aroA mutant, this strain was able to colonize the mouse respiratory tract and to provide full protection after a single intranasal administration. The protection in adult mice was indistinguishable from that induced by two administrations of ⅕ of a human dose of aPV. An important difference, however, was seen in infant mice, where a single administration of BPZE1 fully protected, whereas aPV only offered partial protection. In the context of the difficulties to induce protection in infants with the currently available vaccines early in life, these results provide hope for the development of novel vaccination strategies that may be used in the very young children, possibly at birth. In addition, BPZE1 protected against *B. parapertussis*, whereas aPV did not. Therefore the use of BPZE1 should also have an impact on the incidence of whooping cough caused by *B. parapertussis* in infants.

Although the recent replacement of first generation whole-cell vaccines by new aPV in many countries has significantly reduced the systemic adverse reactions observed with whole-cell vaccines, it has not abolished the need for repeated vaccination to achieve protection. This makes it unlikely to obtain protection in very young children (<6 months) that present the highest risk to develop severe disease. In addition, the wide-spread use of aPV has revealed new, unforeseen problems. Repeated administration of aPV may cause extensive swelling at the site of injection [41], which was not observed with whole-cell vaccines. In approximately 5% of the cases this swelling involves almost the entire limb and lasts for more than a week. Although the mechanism of this swelling has not been characterized yet, it has been proposed to be due to an Arthus hypersensitivity reaction caused by high antibody levels induced by the primary immunization [42]. However, it could also be related to the Th2 skewing of the immune response, as, compared to whole-cell vaccines, aPV administration induces more Th2-type cytokines in vaccinated children [10] and causes a delay in the Th1 development (Mascart et al., in preparation). Delayed maturation of Th1 function has been associated with a risk for atopy in genetically predisposed individuals [33]. The two mechanisms are not mutually exclusive. Compared to aPV, the immune response to BPZE1 administration is less biased towards the Th2 arm, and since BPZE1 is administered mucosally, no swelling reaction can occur.

The use of live attenuated bacteria as vaccines raises the issue of their biosafety. As such, they fall under the directives and guidelines for genetically modified organisms susceptible to be released into the environment. These guidelines and directives describe several objectives that have to be met, including hazard identification and environmental risk assessment [44]. Potential pathogenicity needs to be carefully considered, especially in immuno-compromised individuals, such as those infected with HIV. The natural biology of *B. pertussis* is particularly interesting in that regard. Although pertussis in HIV-infected subjects has been described occasionally, it is rather rare in AIDS patients [45]. In its genetically attenuated form, *B. pertussis* would therefore not be expected to cause major problems in HIV-infected children, especially if severe AIDS is an exclusion criterion, as it is for many vaccines. *B. pertussis* colonization is strictly limited to the respiratory epithelium, without extrapulmonary dissemination of the bacteria, which naturally excludes systemic bacteremia of the BPZE1 vaccine strain. If nevertheless unforeseeable safety problems occurred, the vaccine strain can easily be eliminated by the use of macrolide antibiotics. such as erythromycin, to which essentially all *B. pertussis* isolates are highly sensitive.

A further concern, like for any live vaccine, is the potential release of the vaccine strain in the environment and the consequences of such a release. *B. pertussis* is a strictly human pathogen, and there is no animal vector or reservoir. Moreover, unlike *B. bronchiseptica*, survival of wild-type *B. pertussis* in the environment is extremely limited [46]. Pertussis is only spread by coughing individuals, and there appears to be no asymptomatic carriage [47]. Coughing cannot be assessed in the mouse models used in this study. However, due to the nature of the genetic alterations in BPZE1, in particular the strong reduction of TCT and the genetic inactivation of PTX, this strain would not be expected to induce coughing. Active PTX has been shown to be required for cough induction in a coughing rat model, although the mechanism is not known [48]. If the vaccine strain were nevertheless to be transmitted to non-vaccinated individuals, this would at worst result in increased vaccine coverage. The consequences of each of these potential hazards can thus be graded as negligible and can easily and rapidly be controlled by antibiotic treatment if necessary.

Advantages of the use of BPZE1 include the relatively low production costs, making it especially attractive for developing countries, its needle-free easy and safe mode of administration and its potential to induce mucosal immunity in addition to systemic immunity. Although the role of mucosal immunity against pertussis has surprisingly not been much addressed, the fact that *B. pertussis* is a strictly mucosal pathogen, makes it likely that mucosal immune responses may contribute significantly to protection. None of the currently available vaccines induces any significant mucosal response.

Other advantages of the use of BPZE1 in vaccination are:

the rapid protective immune response obtained after a single intranasal dose of BPZE1, since induction of the immunity can be detected 1 week after vaccination, an increase of the protective immunity over the at least next two months after vaccination, and the complete protective immunity, since a level of protection of more than 99.999% is obtained 2 weeks after vaccination.

The use of live attenuated *B. pertussis* for mucosal vaccination offers yet another advantage. *B. pertussis* can be used for the presentation of heterologous antigens to the respiratory mucosa (for review see 49). The use of BPZE1 as a heterologous expression platform may thus be helpful for the generation of multivalent vaccines against a variety of respiratory pathogens. However, since intranasal delivery of BPZE1 also induces strong systemic immune responses, as shown here by both the high levels of anti-FHA antibodies and of antigen-specific IFN-γ production, it may also be used for the production of antigens to which systemic immune responses are desired.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

REFERENCES

1. WHO (2004) The world health report 2004-changing history, Geneva, WHO.
2. Das P (2002) Whooping cough makes global comeback. Lancet ii: 322.
3. Tan T, Trindade E, Skowronski D (2005) Epidemiology of Pertussis. Pediatr Infect Dis J 24: S10-S18.
4. Centers for Disease Control and Prevention. Epidemiology and Prevention of Vaccine-Preventable Diseases. Atkinson W. Wolfe S, Hamborsky J. McIntyre L, eds. 9$^{th}$ ed. Washington D.C.: Public Health Foundation, 2006; Pertussis Chapter 14.
5. Wirsing von König C H, Halperin S, Riffelmann M, Guiso N (2002) Pertussis of adults and infants. Lancet Infect Dis 2: 744-750.
6. Lewis D B, Yu C C, Meyer J, English B K, Kahn S J, et al. (1991) Cellular and molecular mechanisms for reduced interleukin-4 and interferon-γ production by neonatal T cells. J Clin Invest 87: 194-202.
7. Siegrist C A (2001) Neonatal and early life vaccinology. Vaccine. 19: 3331-3346.
8. Mills K H G (2001) Immunity to *Bordetella pertussis*. Microbes Infect 3: 655-677.
9. Lewis D B, Larsen A, Wilson C B (1986) Reduced interferon-γ mRNA levels in human neonates. J Exp Med 163:1018-1023.
10. Ausiello C M, Urbani F, La Sala A, Lande R, Cassone A (1997) Vaccine- and antigen-dependent type 1 and type 2 cytokine induction after primary vaccination in infants with whole-cell or acellular pertussis vaccines. Infect Immun 65: 2168-2174.
11. Wirsing von König C H, Postels-Multani S, Bock H L, Schmitt H J (1995) Pertussis in adults: frequency of transmission after household exposure. Lancet 346:1326-1329.
12. Mascart F, Verscheure V, Malfroot A, Hainaut M, Piérard D, et al. (2003) *Bordetella pertussis* infection in 2-months-old infants promotes Type 1 T cell responses. J Immunol 170:1504-1509.
13. Menozzi F D, Mutombo R, Renauld G, Gantiez C, Hannah J H, et al. (1994) Heparin-inhibitable lectin activity of the filamentous hemagglutinin adhesin of *Bordetella pertussis*. Infect Immun 62: 769-778.

14. Imaizumi A, Suzuki Y, Ono S, Sato H, Sato Y (1983) Effect of heptakis (2,6-O-dimethyl)-beta-cyclodextrin on the production of pertussis toxin by *Bordetella pertussis*. Infect Immun 41: 1138-1143.
15. Cookson B T, Cho H-L, Herwaldt L A, Goldman W E (1989) Biological activities and chemical composition of purified tracheal cytotoxin of *Bordetella pertussis*. Infect Immun 57: 2223-2229.
16. Alonso S, Pethe K, Mielcarek N, Raze D, Locht C (2001) Role of ADP-ribosyltransferase activity of pertussis toxin in toxin-adhesin redundancy with filamentous hemagglutinin during *Bordetella pertussis* infection. Infect Immun 69: 6038-6043.
17. Collyn F, Lety M A, Nair S, Escuyer V, Ben Younes A. et al. (2002) *Yersinia pseudotuberculosis* harbors a type IV pilus gene cluster that contributes to pathogenicity. Infect Immun 70: 619-620.
18. Mielcarek N, Comette J, Schacht A M, Pierce R J, Locht C, et al. (1997) Intranasal priming with recombinant *Bordetella pertussis* for the induction of a systemic immune response against a heterologous antigen. Infect Immun 65: 544-550.
19. Locht C, Geoffroy M C, Renauld G (1992) Common accessory genes for the *Bordetella pertussis* filamentous hemagglutinin and fimbriae share sequence similarities with the papC and papD gene families. EMBO J. 11: 3175-3183.
20. Sekura R D, Fish F, Manclark C R. Meade B, Zhang Y L (1983) Pertussis toxin. Affinity purification of a new ADP-ribosyltransferase. J Biol Chem 258: 14647-14651.
21. Antoine R, Locht C (1990) Roles of the disulfide bond and the carboxy-terminal region of the S1 subunit in the assembly and biosynthesis of pertussis toxin. Infect Immun 58:1518-1526.
22. Menozzi F O. Gantiez C, Locht C (1991) Interaction of the *Bordetella pertussis* filamentous haemagglutinin with heparin. FEMS Microbiol Lett 62: 59-64.
23. Locht C, Antoine R, Jacob-Dubuisson F (2001) *Bordetella pertussis*, molecular pathogenesis under multiple aspects. Curr Opin Microbiol 4: 82-89.
24. Heiss L N, Flak T A, Lancaster J R, McDaniel M L, Goldman W E (1993) Nitric oxide mediates *Bordetella pertussis* tracheal cytotoxin damage to the respiratory epithelium. Infect Agents Dis 2: 173-177.
25. Goldman W E, Cookson B T (1988) Structure and functions of the *Bordetella* tracheal cytotoxin. Tokai J Exp Clin Med 13 Suppl: 187-191.
26. Locht C, Antoine R (1999) *Bordetella pertussis* protein toxins. In: Alouf J E, Freer J H, editors. Comprehensive sourcebook of bacterial protein toxins. Academic Press, pp. 130-146.
27. Guiso N, Capiau C. Carletti G, Poolman J, Hauser P (1999) Intranasal murine model of *Bordetella pertussis* infection. I. Prediction of protection in human infants by acellular vaccines. Vaccine 17: 2366-2376.
28. Mills K H, Ryan M, Ryan E, Mahon B P (1998) A murine model in which protection correlates with pertussis vaccine efficacy in children reveals complementary roles for humoral and cell-mediated immunity in protection against *Bordetella pertussis*. Infect Immun 66: 594-602.
29. Roduit C, Bozzotti P, Mielcarek N, Lambert P H, Del Giudice G, et al. (2002) Immunogenicity and protective efficacy of neonatal immunization against *Bordetella pertussis* in a murine model: Evidence for early control of Pertussis. Infect Immun 70: 3521-3528.
30. He Q, Viljanen M K. Arvilommi H, Aittanen B, Mertsola J (1998) Whooping cough caused by *Bordetella pertussis* and *Bordetella parapertussis* in an immunized population. JAMA 280: 635-637.
31. Watanabe M, Nagai M (2004) Whooping cough due to *Bordetella parapertussis*: an unresolved problem. Expert Rev Anti Infect Ther 2: 447-454.
32. Mastrantonio P, Stefanelli P, Giuliano M, Herrera Rojas Y, Ciofi degli Atti M. et al. (1998) *Bordetella parapertussis* infection in children: epidemiology, clinical symptoms, and molecular characteristics of isolates. J Clin Microbiol 36: 999-1002.
33. Liese J G. Renner C, Stojanov S. Belohradsky B H. Munich Vaccine Study Group. (2003) Clinical and epidemiological picture of *B. pertussis* and *B. parapertussis* infections after introduction of acellular pertussis vaccines. Arch Dis Child 88: 684-687.
34. Watanabe M, Nagai M (2001) Reciprocal protective immunity against *Bordetella pertussis* and *Bordetella parapertussis* in a murine model of respiratory infection. Infect Immun 69: 6981-6986.
35. Locht C, Bertin P, Menozzi F D, Renauld G (1993) The filamentous haemagglutinin, a multifaceted adhesin produced by virulent *Bordetella* spp. Mol Microbiol 9: 653-660.
36. Huang C C, Chen P M, Kuo J K, Chui W H, Lin S T, et al. (1962) Experimental whooping cough. N Engl J Med 266: 105-111.
37. Bey R F, Shade F J, Goodnow R A, Johnson R C (1981) Intranasal vaccination of dogs with live avirulent *Bordetella bronchiseptica*: correlation of serum aggutination titer and the formation of secretory IgA with protection against experimentally induced infectious tracheobronchitis. Am J Vet Res 42: 1130-1132.
38. De Jong M F (1987) Prevention of atrophic rhinitis in piglets by means of intranasal administration of a live non-AR-pathogenic *Bordetella bronchiseptica* vaccine. Vet Q 9:123-133.
39. Hoiseth S K, Stocker B A D (1981) Aromatic-dependent *Salmonella typhimurium* are non-virulent and effective as live vaccines. Nature 291: 238-239.
40. Roberts M, Maskell D, Novotny P, Dougan G (1990) Construction and characterization in vivo of *Bordetella pertussis* aroA mutants. Infect Immun 58: 732-739.
41. Rennels M B (2003) Extensive swelling reactions occurring after booster doses of diphtheria-tetanus-acellular pertussis vaccines. Semin Pediatr Infect Dis 14: 196-198.
42. Robbins J B, Schneerson R, Trollfors B, Sato H, Sato Y, et al. (2005) The diphtheria and pertussis components of diphtheria-tetanus toxoids-pertussis vaccine should be genetically inactivated mutant toxins. J Infect Dis 191: 81-88.
43. Holt P G, Clough J B, Holt B J, Baron-Hay M J U, Rose A H, et al. (1992) Genetic "risk" for atopy is associated with delayed postnatal maturation of T-cell competence. Clin Exp Allergy 22: 1093-1099.
44. Favre D, Viret J F (2006) Biosafety evaluation of recombinant live oral bacterial vaccines in the context of European regulation. Vaccine. May 1; 24 (18):3856-64.
45. Cohn S E, Knorr K L, Gilligan P H, Smiley M L, Weber D J (1993) Pertussis is rare in human immunodeficiency virus disease. Am Rev Respir Dis 147: 411-413.
46. Porter J F. Wardlaw A C (1993) Long-term survival of *Bordetella bronchiseptica* in lakewater and in buffered saline without added nutrients. FEMS Microbiol Lett 110: 33-36.

47. Linnemann C C Jr. Bass J W. Smith M H D (1968) The carrier state in pertussis. Am J Epidemiol 88: 422-427.

48. Parton R, Hall E, Wardlaw A C (1994) Responses to *Bordetella pertussis* mutant strains and to vaccination in the coughing rat model of pertussis. J Med Microbiol 40: 307-312.

49. Mielcarek N. Alonso S, Locht C (2001) Nasal vaccination using live bacterial vectors. Adv Drug Del Rev 51: 55-69.

50. Lyon R S, Engle J T, Goldman W E. Manuscript in preparation

51. Simon R, Priefer U, Pühler A (1983) A broad host range mobilization system for in vivo genetic engineering: transposon mutagenesis in Gram-negative bacteria. Bio/Technology 1: 784-791.

52. Stibitz S (1994) Use of conditionally counterselectable suicide vectors for allelic exchange. Methods Enzymol 235: 458-465.

53. Antoine R, Huvent I, Chemial K, Deray I, Raze D, et al. (2005) The periplasmic binding protein of tripartite tricarboxylate transporter is involved in signal transduction. J Mol Biol 351: 799-809.

54. Sato H, Ito A, Chiba J, Sato Y (1984) Monoclonal antibodies against pertussis toxin: effect on toxin activity and pertussis infections. Infect Immun 46: 422-428.

55. Sato H, Sato Y, Ito A, Ohishi I (1987) Effect of monoclonal antibody to pertussis toxin on toxin activity. Infect Immun 55: 909-915.

56. Tuomanen, E. And Weiss A. (1985) Characterization of two adhesions of *Bordetella pertussis* for human ciliated respiratory epithelial cells. J. Infect. Dis. 152:118-125.

57. Locht, C., Antoine, R., Veithen A. and Raze D. 2000. Pertussis Toxin: Structure-Function-Relationship. In Aktories K. Just I editors. Handbook of Experimental Pharmacology, Bacterial Protein Toxins. Springer. vol 145, pp. 167-185.

58. Horiguchi Y, Matsuda, H. Koyama H, Nakai T and Kume K. (1992) *Bordetella bronchiseptica* dermonecrotizing toxin suppresses in vivo antibody responses in mice. FEMS Microbiol. Lett. 69:229-234.

59. Bordet et Genysa (1909) L'endotoxine coquelucheuse; Ann. Inst. Pasteur 23: 415-419.

60. Iida & Okonogi (1971) Lieno toxicity of *Bordetella pertussis* in mice; J. Med. Microbiol. 4: 51-61.

61. R. Parton (1985) Effect of prednisone on the toxicity of *Bordetella pertussis* in mice, J. Med. Microbiol. 19: 391-400.

62. Magyar et al (1988) The pathogenesis of turbinate atrophy in pigs caused by *Bordetella bronchiseptica*, Vet. Microbiol. 3: 1719-1728.

63. Roop et al (1987) Virulence factors of *Bordetella bronchiseptica* associated with the production of infectious atropic rhinitis and pneumonia in experimentally infected neonatal swine, Infect. Immun. 55: 217-222.

64. Weiss & Goodman (1989) Lethal infection by *Bordetella pertussis* mutants in the infant mouse model, Infect. Immun. 57: 3757-3764.

65. Allan & Maskell (1996) The identification, cloning and mutagenesis of a genetic locus required for lipopacysaccharide biosynthesis in *Bordetella pertussis*, Mol. Microbiol. 19: 37-52.

66. Alonso et al (2002) Eighty kilodalton N-terminal moiety of *Bordetella pertussis* filamentous hemagglutinin: adherence, immunogenicity, and protective role, Infection & Immunity. 70, 4142-4147.

67. Cummings, C. A., Bootsma, H. J., Relman D. A. and Miller J. F. (2006) Species- and Strain-specific Control of a Complex, Flexible Regulon by *Bordetella* BvgAS. J. Bacteriol. 188:1775-1785.

68. Kashimoto T., Katahira J, Cornejo W R, Masuda M, Fukuoh A, Matsuzawa T, Ohnishi T, Horiguchi Y. (1999) Identification of functional domains of *Bordetella* dermonecrotizing toxin. Infect. Immun. 67 (8) 3727-32.

What is claimed is:

1. An immunogenic composition comprising a pharmaceutically acceptable carrier and a dose of a live attenuated *Bordetella pertussis* strain which is able to colonize a subject when administered to the subject, wherein the live attenuated *Bordetella pertussis* strain has its native *Bordetella pertussis* ampG gene replaced with a heterologous ampG gene wherein the replacement of the *Bordetella pertussis* ampG gene with the heterologous ampG gene causes the *Bordetella pertussis* strain to express less than 5% of the tracheal cytotoxin (TCT) activity as that expressed by a *Bordetella pertussis* strain which does not have its native *Bordetella pertussis* ampG gene replaced with the heterologous ampG gene.

2. The immunogenic composition of claim 1, wherein the live attenuated *Bordetella pertussis* strain comprises a heterologous expression platform which carries a heterologous antigen.

3. The immunogenic composition of claim 2, wherein the heterologous antigen is one expressed by a respiratory pathogen selected from the group consisting of: *Neisseria, Pneumophila, Yersinia, Pseudomonas, Mycobacteria*, and *Influenza.*

4. The immunogenic composition of claim 1, wherein the immunogenic composition is formulated as a powder.

5. The immunogenic composition of claim 1, wherein the immunogenic composition is formulated as a liquid.

6. The immunogenic composition of claim 1, wherein the immunogenic composition is formulated as a gel.

* * * * *